US012685478B2

(12) United States Patent　　　(10) Patent No.:　US 12,685,478 B2
Leuthardt et al.　　　　　　　　(45) Date of Patent:　　　Jul. 21, 2026

(54) GENERATING FUNCTIONAL BRAIN MAPPINGS AND ACCOMPANYING REFERENCE INFORMATION

(71) Applicant: SORA NEUROSCIENCE, INC., Minneapolis, MN (US)

(72) Inventors: Eric C. Leuthardt, St. Louis, MO (US); Connor J. Burns, Louisville, KY (US); Patrick R. Campbell, Maryville, TN (US); Carl D. Hacker, St. Louis, MO (US); Stephen R. Schaefer, Minneapolis, MN (US)

(73) Assignee: SORA NEUROSCIENCE, INC., Minneapolis, MN (US)

( * ) Notice: Subject to any disclaimer, the term of this patent is extended or adjusted under 35 U.S.C. 154(b) by 283 days.

(21) Appl. No.: 18/352,163

(22) Filed: Jul. 13, 2023

(65) Prior Publication Data

US 2024/0016439 A1　　　Jan. 18, 2024

Related U.S. Application Data

(60) Provisional application No. 63/368,358, filed on Jul. 13, 2022.

(51) Int. Cl.
| | |
|---|---|
| *G06T 7/00* | (2017.01) |
| *A61B 5/00* | (2006.01) |
| *A61B 5/055* | (2006.01) |
| *G01R 33/48* | (2006.01) |
| *G01R 33/56* | (2006.01) |

(52) U.S. Cl.
CPC .......... *A61B 5/4064* (2013.01); *A61B 5/0042* (2013.01); *A61B 5/055* (2013.01);
(Continued)

(58) Field of Classification Search
CPC ..... A61B 5/4064; A61B 5/0042; A61B 5/055; A61B 5/0013; A61B 5/0263;
(Continued)

(56) References Cited

U.S. PATENT DOCUMENTS

| | | | | |
|---|---|---|---|---|
| 9,662,039 | B2 * | 5/2017 | Liu ........................ | A61B 5/055 |
| 11,589,826 | B2 * | 2/2023 | Leuthardt .............. | A61B 5/055 |

(Continued)

OTHER PUBLICATIONS

International Search Report and Written Opinion of the ISA/EP, mailed Nov. 9, 2023, in PCT Application No. PCT/US2023/070172, 15 pages.
(Continued)

*Primary Examiner* — Juan M Guillermety
(74) *Attorney, Agent, or Firm* — Barta Jones, PLLC

(57)　　　　　ABSTRACT
A method for mapping functionally related brain regions of a subject. The method includes receiving a structural brain image and a dataset of resting-state functional MRI (rs-fMRI) three-dimensional (3D) image frames of a brain of the subject includes 3D image frames of the subject's brain over time. A functional connectivity map identifying groupings of functionally connected voxels is overlaid on the structural brain image. Spontaneous brain activations associated with each voxel in a grouping of functionally connected voxels are time-correlated with spontaneous brain activations in one or more other voxels in the grouping of functionally connected voxels. A reference location map for a pre-defined resting state network is generated, including reference information output. The reference location map includes brain reference locations that are informative of the one or more resting-state networks to assist a user in identifying the resting state network of the functional connectivity map.

20 Claims, 16 Drawing Sheets

(52) U.S. Cl.
CPC ..... *G01R 33/4806* (2013.01); *G01R 33/5608* (2013.01); *G06T 7/00* (2013.01); *G06T 2207/20081* (2013.01); *G06T 2207/30016* (2013.01)

(58) Field of Classification Search
CPC ............... A61B 5/7264; A61B 5/7267; G01R 33/4806; G01R 33/5608; G06T 7/00; G06T 2207/20081; G06T 2207/30016; G06T 2207/10016; G06T 2207/10096; G06T 2207/20084; G06T 7/0016; G16H 30/40; G16H 50/70; G16H 20/40; G16H 50/20

See application file for complete search history.

(56) References Cited

U.S. PATENT DOCUMENTS 11,776,128 B2 * 10/2023 Yoo ...................... G06T 7/0012
382/131

| | | | | |
|---|---|---|---|---|
| 2013/0231552 | A1* | 9/2013 | Grady .................. G06T 7/0012 600/410 |
| 2017/0300622 | A1* | 10/2017 | Laviolette ............. G06T 7/0014 |
| 2019/0142338 | A1* | 5/2019 | Fang ...................... A61B 5/055 600/408 |
| 2020/0167914 | A1* | 5/2020 | Stamatoyannopoulos ................. G06T 7/0012 |
| 2020/0237316 | A9 | 7/2020 | Leuthardt |
| 2023/0115330 | A1* | 4/2023 | Hermosillo ........... A61B 5/055 607/45 |

OTHER PUBLICATIONS

Lv et al.; Resting-State Functional MRI: Everything That Nonexperts Have Always Wanted to Know, American Journal of Neuroradiology; Aug. 31, 2018, XP093095608, 11 pages.
Hacker et al.; Resting state network estimation in individual subjects, Neuroimage, vol. 82, Jun. 2, 2013, pp. 616-633, XP028705597.
Communication pursuant to Article 94(3) EPC, by the EPO, dated Apr. 21, 2026, in Application No. 23754066.1, 7 pages.

* cited by examiner

100

INPUT: Multiple Sets of Voxel-wise Spontaneous
Brain Activation Intensity Values

Generate Voxel-wise Correlation Map for Spontaneous
Brain Activations

Apply Voxel-wise Correlation Map to Nonadaptive MLP
Algorithm

Transform Voxel Raw Identity Scores (Raw MLP Output) to
Functional Group Membership Estimation Percentiles

OUTPUT: Functional Connectivity Maps
(Unlabeled as to their Specific Functions)

*FIG. 7*

GENERATING FUNCTIONAL BRAIN MAPPINGS AND ACCOMPANYING REFERENCE INFORMATION

CROSS-REFERENCE TO RELATED APPLICATION

This application claims priority to U.S. Provisional Patent Application No. 63/368,358, entitled "GENERATING FUNCTIONAL BRAIN MAPPINGS AND ACCOMPANYING REFERENCE INFORMATION," filed on Jul. 13, 2022, the disclosure of which is incorporated herein by reference in its entirety.

FIELD OF DISCLOSURE

The techniques described in this document relate to software-based systems, for example, artificial intelligence, machine learning based systems, used to generate functional brain mappings.

BACKGROUND

An example software-based system to which the techniques described in this document relate is a system that maps functional brain networks in an individual subject's brain using image data acquired for the subject's brain, for example, magnetic resonance imaging (MRI) data. Mapping functional brain networks is useful in a wide array of clinical applications, for example, in brain surgery planning and decision support in the operating room, in psychiatric and/or brain disease diagnostics, and in identifying target locations in the brain for brain disease treatments, as well as uses in research and education.

Functional MRI (fMRI) is a form of MRI that detects information reflective of neural activity. In conventional task-based fMRI (tb-fMRI), certain brain functions may be localized by presenting stimuli or imposing tasks (such as finger tapping or object naming) to a subject in an MRI scanner, or in other words, during the time that fMRI data are being acquired from the subject. Using fMRI data, the locations of the brain involved in performing the "task" may be identified. These functional brain mappings are often referred to as "task activation maps."

Another way brain functions may be localized is using resting state fMRI (rs-fMRI). In rs-fMRI, the subject lies in the MRI scanner in a state of rest, without external stimuli being presented to the subject and/or the patient performing tasks. In doing so, the acquired fMRI data reveals information about the brain's spontaneous, or endogenous, brain activations. It is known that different locations of the brain involved in performing the same cognitive function have spontaneous brain activations that are time correlated with one another, or in other words, occur synchronously. This physiological feature of the brain wherein spontaneous brain activity is synchronous in functionally related parts of the brain is referred to as "functional connectivity." As such, rs-fMRI data may be used to create functional brain network mappings, without tasks or external stimuli being needed during the MRI scan session.

Regions which exhibit strong functional connectivity (that is, temporally correlated physiological events) when the brain is at rest are referred to as resting state networks (RSNs). RSNs are organized hierarchically and can be readily sub-divided to focus in one area or another. Nonetheless, researchers reached consensus in the early 2010s concerning the number (7±1) and general organization of top-level RSNs making up a topology or schema of RSNs.

Using rs-fMRI data, it is conventional to map a functional brain network, or RSN, by first identifying a reference location, or "seed," that is a part of a known functional network. Then, using the seed as a reference point, it is possible to identify other locations of the brain having spontaneous brain activity that is synchronous with the spontaneous brain activity at the location of the reference seed. As such, it is possible to generate mappings of functional brain networks. Such mappings may be referred to as "functional connectivity" maps. As an example, with a reference seed being placed at a location of the brain known to be a part of a defined sensorimotor network ("SMN"), it is possible to identify other locations of the brain wherein spontaneous brain activity is synchronous with spontaneous brain activity at the seed location, and as such, generate a functional connectivity mapping of the patient's SMN network. Various other functional networks may be mapped similarly using other seed locations that are specific to other functional networks.

Artificial intelligence machine learning techniques have been applied to the process of generating functional connectivity mappings from rs-fMRI datasets. For example, as described in U.S. Pat. No. 9,480,402 to Leuthardt et al., a machine learning based system processes rs-fMRI scan data for a subject and maps the patient's brain into defined functional networks in accordance with a defined topology or schema of brain networks.

SUMMARY

Some examples of the disclosure provide systems and methods for generating primary system outputs along with an accompanying output of reference information. The primary system output is generated using a machine-learning based algorithm created using training data. The accompanying reference information output is informative of the training data used to create the machine-learning based algorithm.

In various embodiments, the primary system output is a mapping of defined functional brain networks within the brain of an individual subject, generated based upon image data pertaining to the individual subject's brain. This mapping may be overlaid upon a structural image of the brain of individual subject. The accompanying output of reference information may comprise population-averaged location information for the defined functional brain networks. The population-averaged location information may include, for each defined network, a set of population-averaged reference locations falling within the defined network. These population-averaged reference locations may be utilized in defining training data sets for training the machine-learning based algorithm used in the generation of the primary system outputs. The sets of population-averaged reference locations may be overlaid upon a structural image of a brain, which may be a structural image of the brain of the individual subject for which the primary system output is generated.

In various embodiments, one or more of the following features may be included. The image data upon which the functional brain network mapping is based may be functional magnetic resonance imaging (fMRI) data, which may be resting-state fMRI (rs-fMRI) data acquired during a time the subject is lying in the MRI scanning equipment in in a state of rest. The defined functional brain networks to which the mapping is directed may be a defined set of one or more resting state networks (RSNs) making up a defined topology of RSNs. The defined set of RSNs included in the topology may be macro-scale, or in other words top-level, RSNs present within a broad range of subjects, for example, healthy subjects. The number of macro-scale RSNs included in the topology of RSNs may equal six to eight RSNs, and in some cases, include seven RSNs. In some examples, the macro-scale RSNs include brain networks making up the eloquent cortex of the subject's brain. For example, the RSNs making up the eloquent cortex and included in the RSN topology may include a sensorimotor network (SMN) and a language network (LAN). For the eloquent cortex, the defined topology of RSNs may also include a vision network (VIS). Additionally, or alternatively, the macro-scale RSNs included in the topology may comprise one or more of a ventral attention network (VAN), a dorsal attention network (DAN), a frontoparietal control network (FPC), and a default mode network (DMN). Other topologies and other RSNs at various levels of the brain network hierarchy may be defined.

In some embodiments, the primary system output is a set of functional connectivity maps. In this example, each functional connectivity map in the set may identify, based upon the individual subject's rs-fMRI scan data, functionally connected voxels of the individual subject's brain included in a different one RSN of the topology of defined RSNs. In some examples, a voxel is a 3D section of brain tissue.

The generation of functional connectivity maps may include generating, based upon the rs-fMRI data for the individual subject, a voxel-wise correlation map of the individual subject's brain comprising measures of correlation between MR signals at different voxel pairs throughout the brain. Generation of the voxel-wise correlation map may include calculating, for each voxel pair, a Pearson product-moment correlation coefficient for the MR signal at one voxel compared to the MR signal at a second voxel. In this example, the calculation of the correlation coefficient may yield a single scalar value representing a measure of strength in linear association between the two MR signals of the voxel pair. The generation of functional connectivity maps may also include assigning voxels of the individual subject's brain to the defined RSNs of the topology of RSNs. The assignment of voxels to the defined RSNs may involves use of the machine-learning based algorithm.

In various embodiments, the machine-learning based algorithm may be trained, using a supervised learning process, to assign voxels using pattern matching that applies weight in determining the assignment to the following factors: (i) within-network MR signal patterns being correlated in time, and (ii) global patterns in MR signals throughout the brain and between different networks. The supervised learning process may use, for each RSN of the topology of RSNs, a set of reference locations in the brain representing population-based locations that fall within the RSN. The supervised learning process may also use rs-fMRI datasets acquired from a number of individual subjects, and may also include generating, based upon the rs-fMRI data of one rs-fMRI dataset, a voxel-wise correlation map of the individual subject's brain comprising measures of correlation between MR signals at different voxel pairs throughout the brain. The supervised learning process may also include generating a number of supervised training datasets for each rs-fMRI dataset, wherein the datasets include: (i) the voxel-wise correlation map information for voxel locations corresponding to the reference locations, and (ii) for supervision, network assignment information comprising the RSN identity to which the voxel location corresponding to the reference location is a member.

In various embodiments, the output reference information may include a set of RSN reference maps, one for each RSN of the topology of RSNs, wherein each RSN reference map includes the corresponding set of reference locations in the brain representing population-based locations that fall within the RSN. Each RSN reference map may include the reference locations for a particular RSN overlaid upon an anatomical brain image. The anatomical brain image upon with the RSN reference locations are overlaid may be an anatomical brain image of the same individual subject for which output RSN mappings are generated.

Other examples of the disclosure provide a method for overlaying functionally related brain regions of subjects. A structural magnetic resonance imaging (MRI) brain image associated with a subject and a dataset of resting-state functional MRI (rs-fMRI) three-dimensional (3D) image frames of a brain of the subject are received. The dataset includes a plurality of 3D image frames over time. A plurality of reference location maps for each pre-defined resting state network in a plurality of pre-defined resting state networks are overlaid on the structural MRI brain image of a subject to generate a plurality of reference location maps. Each population-level map is overlaid on an instance of the structural MRI brain image of the subject such that a single reference location map is overlaid on a given instance of the structural MRI brain image.

Other examples provide a method for overlaying functionally related brain regions of subjects. A structural magnetic resonance imaging (MRI) brain image associated with a subject and a dataset of resting-state functional MRI (rs-fMRI) three-dimensional (3D) image frames of a brain of the subject are received. The dataset includes a plurality of 3D image frames over time. One or more functional connectivity maps identifying one or more groupings of functionally connected voxels are overlaid on the structural MRI brain image of the subject. A single functional connectivity map is overlaid on each separate copy of the structural MRI of the subject. The functional connectivity maps are generated based on the dataset of rs-fMRI image frames. Spontaneous brain activations associated with each voxel in a selected grouping of functionally connected voxels in each functional connectivity map are time-correlated with spontaneous brain activations in one or more other voxels in the selected grouping of functionally connected voxels.

Another aspect of the disclosure provides a method for overlaying functionally related brain regions of subjects. A structural magnetic resonance imaging (MRI) brain image associated with a subject and a dataset of resting-state functional MRI (rs-fMRI) three-dimensional (3D) image frames of a brain of the subject are received. The dataset includes a plurality of 3D image frames over time. One or more functional connectivity maps identifying one or more groupings of functionally connected voxels are overlaid on the structural MRI brain image of the subject. A single functional connectivity map is overlaid on each separate copy of the structural MRI of the subject. A single functional connectivity map is overlaid on a single instance of the structural MRI. In each functional connectivity map, spontaneous brain activations associated with each voxel in a selected grouping of functionally connected voxels are time-correlated with spontaneous brain activations in one or more other voxels in the selected grouping of functionally connected voxels. A plurality of population-level reference location maps for each pre-defined resting state network in a plurality of pre-defined resting state networks are overlaid on the structural MRI brain image of a subject. Each population-level reference location map is overlaid on a copy of the structural MRI brain image of the subject, such that a functional connectivity map and a population-level reference location map is overlaid on each structural MRI brain image copy.

BRIEF DESCRIPTION OF THE DRAWINGS

FIG. 7 is an exemplary flow chart illustrating functional connectivity analysis.

Corresponding reference characters indicate corresponding parts throughout the drawings.

DETAILED DESCRIPTION

Figure 1:
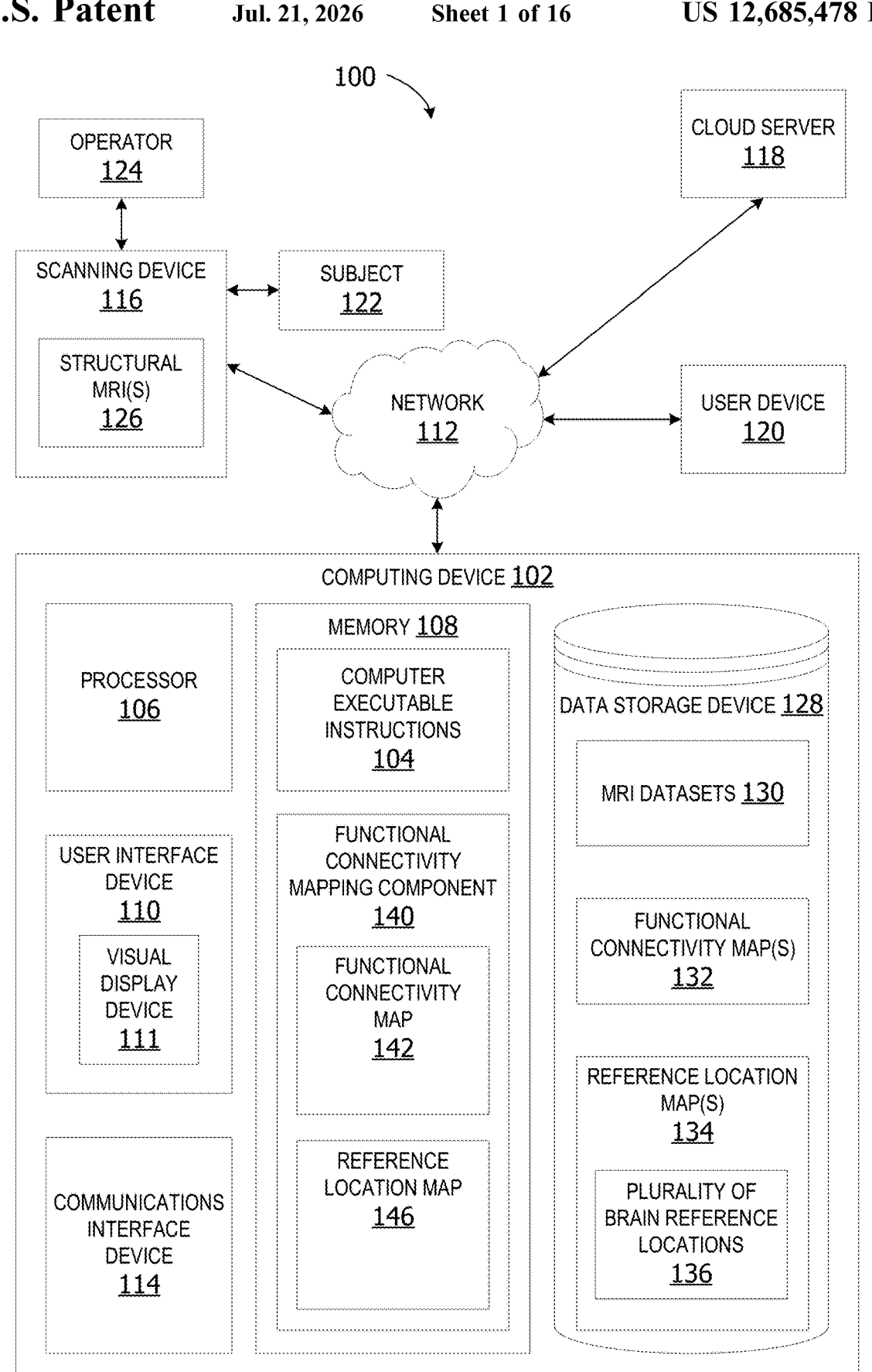
FIG. 1 is an exemplary block diagram illustrating a system for mapping functionally related brain regions of a subject on a structural magnetic resonance image (MRI) associated with the subject.

A more detailed understanding can be obtained from the following description, presented by way of example, in conjunction with the accompanying drawings. The entities, connections, arrangements, and the like that are depicted in, and in connection with the various figures, are presented by way of example and not by way of limitation. As such, any and all statements or other indications as to what a particular figure depicts, what a particular element or entity in a particular figure is or has, and any and all similar statements, that can in isolation and out of context be read as absolute and therefore limiting, can only properly be read as being constructively preceded by a clause such as "In at least some examples, . . . " For brevity and clarity of presentation, this implied leading clause is not repeated ad nauseum.

A software-based application system, in one embodiment, maps functional brain networks in an individual subject's brain using image data acquired for the subject's brain, for example, functional magnetic resonance imaging (fMRI) data. In addition, the application system may also generate reference information to accompany the system's network mapping outputs. The reference information may be designed to provide insight into the design and operation of the software-based system. The software-based system may be an artificial intelligence, machine learning based system utilizing an algorithm with hyperparameters and weights generated during an algorithm training process using training data. In that case, the reference information providing insight into the system design and operation of the system may, for example, include information regarding or describing the nature of the training data used to create machine-learned algorithm parameters and weights. The generation of reference information to accompany system outputs may aid a user's interpretation and understanding of the outputs. Alternatively, or additionally, the reference information may provide baseline information for functional networks in healthy subjects, and thus provide a point of comparison for the brain network mapping outputs.

The software-based system, in one example, uses fMRI data for a subject, which data are acquired before operation of the software-based system. During an fMRI scan session of a subject, an MRI scanning device is used to acquire blood oxygen level dependent (BOLD) magnetic resonance (MR) signals at locations throughout the brain of the subject and at successive points in time. Each MR signal provides an instantaneous measure of oxygen level at a specific time and location in the brain. An increase in the BOLD MR signal over time at a specific location in the brain indicates the presence of a hemodynamic response (HDR) triggered by nearby neuronal activity. The triggering neuronal activity precedes the HDR by about 4-6 seconds, given it takes time for the vascular system to respond to the brain's need for glucose. The need for glucose is caused by the expenditure of glucose during neuronal activity, and glucose is delivered via increased blood flow resulting in the increased oxygen level detectable by BOLD MR. When the HDR resulting from the neuronal activity ends, the magnitude of the BOLD MR signal reduces and settles to a baseline level indicative of no nearby neuronal activity.

Task-based fMRI (tb-fMRI) data acquisition can be used to obtain information about brain activations that are stimulated by intentional thoughts and action or by an outside stimulus presented to the subject. In a typical tb-fMRI scan session, the stimulation may be caused by the subject being instructed to perform a task such as a finger tapping exercise, or by a stimulus being presented to a subject such as a visual display of a checkerboard shown before the subject's eyes during the course of the fMRI session. For task-based fMRI studies, software can be used to evaluate where the MRI signal has changed in a time correlation with when the stimulus, or "task," occurred. This software processing generates what is typically called a task activation map.

In a different imaging modality called resting-state fMRI (rs-fMRI), a subject lies in an MRI scanning system in a state of rest. The subject does not perform tasks in the MRI scanner. The subject may be instructed to keep their eyes open and remain in a state of quiet wakefulness while fixating on a visual crosshair projected in front of their eyes in the MRI scanner. As such, resting-state fMRI differs from the traditional task-based fMRI method in which the subject performs tasks or is presented with stimuli in the MRI scanning device.

Resting-state fMRI is used to obtain information about brain activations that are spontaneously, e.g., endogenously, generated in the subject's brain (e.g., brain activations that are not stimulated by intentional subject thoughts and action or by an outside stimulus). It has been found that spontaneous brain activations are not simply random noise, but rather are time-correlated within, and throughout, functionally related parts of the brain. The spontaneous brain activations are not time-correlated between different functional parts of the brain. This time-correlation physiological characteristic is commonly referred to in the field of brain fMRI as "functional connectivity."

It has been shown that the time-correlation characteristic of functionally connected spontaneous brain activations are associated with time courses of low frequency (<0.1 Hz) fluctuations in BOLD MR in the resting brain. These spontaneous brain activations can be shown to have a high degree of correlation ($P<10^{-3}$) within the motor control brain region, which can be identified through a separate task-based fMRI evaluation. The correlation of low-frequency fluctuations in BOLD magnetic resonance (MR) signals may be a manifestation of functional connectivity of the brain. The time-correlated nature of the low-frequency fluctuations in spontaneous brain activity applies not only to activations within the motor control functional network but to activations within other functionally related brain networks. Accordingly, spontaneous BOLD activity is not random noise, but is specifically organized in the resting human brain. Under resting conditions, the brain is frequently engaged in spontaneous activity that is not attributable to specific inputs or output generation. This type of spontaneous activity originates within the brain intrinsically forming a plurality of predefined resting state neural networks.

Different locations of the human brain which exhibit strong functional connectivity (i.e., temporally correlated spontaneous brain activation physiological events) when the brain is at rest are referred to as resting state networks (RSNs). RSNs are organized hierarchically and can be readily sub-divided to focus in one area or another. Research on functional connectivity using resting-state fMRI data has reached a consensus that functional connectivity networks organize into a topology of seven (plus or minus one) major functional brain networks. In different topologies, there may be differences in nomenclature for referring to the network, differences in which cognitive functions are grouped into the same functional network, and differences in a combined network being defined as one or two networks. Despite those differences among network topologies at the top level, there is general consensus that the number of networks is eight, plus or minus one, network.

To define a network topology, statistical "clustering" tools can be used to locate clusters present in the timing of spontaneous brain activations across a broad population of subjects. Given that spontaneous brain activations are time correlated within functionally connected parts of the brain, the "clusters" found in the timing of spontaneous brain activations correspond to specific brain functions that can be found from resting-state fMRI data.

Referring to the figures, an example software-based application system is shown that maps functional brain networks in an individual subject's brain using image data acquired for the subject's brain, namely, structural, and functional MRI data. The application system also generates, in this example, reference information to accompany the system's functional network map outputs. The reference information is designed to provide insight into the design and operation of the software-based system. In this example, the software-based system is an artificial intelligence, machine learning based system utilizing an algorithm with hyperparameters and weights generated during an algorithm training process using training data. The reference information generated by the system includes information regarding or describing the nature of the training data used to create machine-learned algorithm parameters and weights. More specifically, the system enables customized overlays of functionally related brain regions of subjects. In some examples, a functional connectivity processing component combines a structural magnetic resonance imaging (MRI) brain image of a subject with a functional connectivity map overlay and/or a reference location map having a plurality of brain reference locations that are informative of a resting state network being mapped. In this manner, a customized mapping of functionally related brain regions of a subject is provided for improved mapping and accuracy identifying pre-defined resting state networks. The generation of reference information to accompany system outputs may aid a user's interpretation and understanding of the outputs. Alternatively, or additionally, the reference information may provide baseline information for functional networks in healthy subjects, and thus provide a point of comparison for the brain network mapping outputs.

In this and other examples, the functional connectivity processing component is software as a medical device (SaMD) intended to be operated by trained radiology users (radiologists with the assistance of Radiologic Technologists under their supervision), and its output maps overlaid on structural brain images of a subject are intended for use by physicians to support the interpretation and evaluation of examinations of the brain within healthcare institutions, for example, in radiology, neuroradiology and neurosurgery environments, for improved user experience.

In some examples, the functional connectivity processing component may be a radiology tool that reflects its use in analyzing information from specific magnetic resonance (MR) imaging sequences. It may be used for evaluation of blood oxygen level dependent (BOLD) magnetic resonance (MR) images for the routine use in MR image viewing. This host computing platform-based software option with dedicated MR specific workflows provides MR specific evaluation tools that supports interpretation and evaluation of examinations within healthcare institutions.

Aspects of the disclosure further enable provision of reference location map overlays for functional connectivity maps on per-subject structural MRI brain images enabling faster and more accurate identification of resting state networks. The computing device operates in an unconventional manner by overlaying structural MRI brain images of individual subjects with reference locations maps and/or functional connectivity maps. In this manner, the computing device is used in an unconventional manner, and allows improved understanding and interpretation of mappings of functionally related brain regions of a subject. The mapping functional connectivity processing component outputs mapping overlays used to create customized structural MRI brain images of a specific individual or standardized subject having overlaid functional connectivity mapping and/or reference location mapping, thereby improving the functioning of the underlying computing device.

Referring again to FIG. 1, an exemplary block diagram illustrates a system 100 for mapping functionally related brain regions of subject using one or more overlays on a structural magnetic resonance image (MRI) associated with a subject. In the example of FIG. 1, the computing device 102 represents any device executing computer-executable instructions 104 (e.g., as application programs, operating system functionality, or both) to implement the operations and functionality associated with the computing device 102. The computing device 102 in some examples includes a mobile computing device or any other portable device. A mobile computing device includes, for example but without limitation, a mobile telephone, laptop, tablet, computing pad, netbook, gaming device, and/or portable media player. The computing device 102 can also include less-portable devices such as servers, desktop personal computers, kiosks, or tabletop devices. Additionally, the computing device 102 can represent a group of processing units or other computing devices.

In some examples, the system or computing device 102 has at least one processor 106 and memory 108. The computing device 102 in other examples includes a user interface device 110.

The processor 106 includes any quantity of processing units and is programmed to execute the computer-executable instructions 104. The computer-executable instructions 104 is performed by the processor 106, performed by multiple processors within the computing device 102 or performed by a processor external to the computing device 102. In some examples, the processor 106 is programmed to execute instructions such as those illustrated in the figures (e.g., FIG. 4, FIG. 5, FIG. 6, FIG. 7, and FIG. 8).

The computing device 102 further has one or more computer-readable media such as the memory 108. The memory 108 includes any quantity of media associated with or accessible by the computing device 102. The memory 108, in these examples, is internal to the computing device 102 (as shown in FIG. 1). In other examples, the memory 108 is external to the computing device (not shown) or both (not shown). The memory 108 can include read-only memory and/or memory wired into an analog computing device.

The memory 108 stores data, such as one or more applications. The applications, when executed by the processor 106, operate to perform functionality on the computing device 102. The applications can communicate with counterpart applications or services such as web services accessible via a network 112. In an example, the applications represent downloaded client-side applications that correspond to server-side services executing in a cloud.

In other examples, the user interface device 110 includes a graphics card for displaying data to the user and receiving data from the user. The user interface device 110 can also include computer-executable instructions (e.g., a driver) for operating the graphics card. Further, the user interface device 110 can include a display (e.g., a touch screen display or natural user interface) and/or computer-executable instructions (e.g., a driver) for operating the display. The user interface device 110 can also include one or more of the following to provide data to the user or receive data from the user: speakers, a sound card, a camera, a microphone, a vibration motor, one or more accelerometers, a BLUETOOTH® brand communication module, global positioning system (GPS) hardware, and a photoreceptive light sensor. In some examples, the user interface device 110 includes a visual display device 111 for displaying data, such as, but not limited to, image(s). The image(s) displayable on display device 111 optionally include brain images including mapping overlays.

The network 112 may be implemented by one or more physical network components, such as, but without limitation, routers, switches, network interface cards (NICs), and other network devices. The network 112 may be any type of network for enabling communications with remote computing devices, such as, but not limited to, a local area network (LAN), a subnet, a wide area network (WAN), a wireless (Wi-Fi) network, or any other type of network. In this example, the network 112 is a WAN, such as the Internet. However, in other examples, the network 112 may be a local or private LAN.

In some examples, the system 100 optionally includes a communications interface device 114. The communications interface device 114 may include a network interface card and/or computer-executable instructions (e.g., a driver) for operating the network interface card. Communication between the computing device 102 and other devices, such as but not limited to, a scanning device 116, a cloud server 118 and/or a user device 120, can occur using any protocol or mechanism over any wired or wireless connection. In some examples, the communications interface device 114 is operable with short range communication technologies such as by using near-field communication (NFC) tags.

The user device 120 represents any device executing computer-executable instructions. The user device 120 can be implemented as a mobile computing device, such as, but not limited to, a wearable computing device, a mobile telephone, laptop, tablet, computing pad, netbook, gaming device, and/or any other portable device. The user device 120 includes at least one processor and a memory. The user device 120 can also include a user interface device. In some examples, generated image(s) may be displayed at the user device 120 for presentation or viewing by a user associated with the user device 120.

The cloud server 118 is a logical server providing services to the computing device 102 or other clients, such as, but not limited to, the user device 120. The cloud server 118 may be hosted and/or delivered via the network 112. In some non-limiting examples, the cloud server 118 may be associated with one or more physical servers in one or more data centers. In other examples, the cloud server 118 may be associated with a distributed network of servers. In some examples, the computing device 102 outputs brain image(s) and/or map overlays to the cloud server 118 for storage and/or further analysis.

The scanning device 116 may be a device for scanning a brain of a subject 122. The scanning device 116 generates one or more brain images of the brain of the subject. In some examples, the scanning device 116 is a magnetic resonance imaging (MRI) machine for generating MRI(s) of the subject when operated by an operator 124, such as a technician or other imaging specialist. In this example, the scanning device 116 generates one or more structural MRI(s) 126 of the subject 122 as well as one or more functional MRIs of the brain of the subject taken over a period of time.

The system 100 may include a data storage device 128 for storing data, such as, the input and output data of the system's processing. This includes, but is not limited to, MRI datasets 130 for subjects, which, in one example.

includes both structural MRI data for a subject and fMRI data for the subject (and specifically in this example, rs-fMRI data). An MRI dataset serves as input data for the system's processing. The rs-fMRI data may include one or more fMRIs scans generated by the scanning device 116 while the subject 122 is in a resting state. The data storage device 128 may also store outputs of system processing, namely, sets of functional connectivity map(s) 132 for individual subjects and corresponding sets of reference location map(s) 134 that map reference brain locations 136 for each network onto an individual subject's structural brain image.

In a conventional embodiment deployed in a radiology department, data storage device 128 may be part of a picture archiving and communication system (PACS). The data storage device 128 can include one or more different types of data storage devices, such as, for example, one or more rotating disks drives, one or more solid state drives (SSDs), and/or any other type of data storage device. The data storage device 128, in some non-limiting examples, includes a redundant array of independent disks (RAID) array. In other examples, the data storage device 128 includes a database.

The data storage device 128 is illustrated as being included within the computing device 102, attached to the computing device, plugged into the computing device, or otherwise associated with the computing device 102. In other examples, the data storage device 128 may be remote data storage accessed by the computing device via the network 112, such as a remote data storage device, a data storage in a remote data center, or a cloud storage.

In other examples, the scanning device 116 includes a set of one or more imaging devices, such as an MRI scanning device. The scanning device can provide real-time brain imaging of the subject 122 and/or image data recording. The scanning device 116, in this example, sends MRI scanning data, such as one or more MRIs, to the functional connectivity mapping component 140 via the network 112.

In some examples, the computing device 102 includes a functional connectivity mapping component 140 that includes a machine learning (ML) based algorithm component. The ML based algorithm component may include pattern recognition, modeling, or other machine learning algorithms to analyze MRI data and/or predefined resting state network data to generate functional connectivity maps, such as, but not limited to, the functional connectivity map 142 that comprise brain volume elements (voxels) included in a network overlaid upon a structural image of the subject's brain.

The memory 108 in some examples stores the functional connectivity mapping component 140, which, when executed by the processor 106 of the computing device 102, receives a MRI dataset for a subject that includes a structural MRI brain image and an rs-fMRI dataset, and generates (i) a set of functional connectivity maps 142, one map for each RSN of the network topology and each map showing the voxels of the subject's brain included in a particular RSN overlaid on a structural image of the subject; (ii) a corresponding set of reference maps 146, one map for each RSN of the network topology and each map showing reference locations for a particular RSN (for example, population-averaged locations in healthy subjects that fall within the particular RSN) overlaid on a structural image of the subject; and (iii) a quality control report.

In one example, the system 102 uses a standardized topology, or schema, of seven well-defined primary brain functions or resting state networks (RSNs). The seven predefined RSNs in one example includes the visual network (VIS), somatomotor network (SMN), dorsal attention network (DAN), ventral attention network (VAN), language network (LAN), frontoparietal control network (FPC), and default mode networks (DMN). In other topologies, different RSN may be defined, and in cases of RSN topologies at a lower level of hierarchy, a topology may be used that includes many more networks, for example, topologies of 10 networks and 17 networks are commonly used, based on clustering studies that show networks on a population level fall into these numbers of networks on a consistent basis at a lower level in the hierarchy.

A functional connectivity map generated from rs-fMRI analysis shows the location in the subject of each of the defined functional networks of the brain function topology. In other words, a single grouping of functionally connected brain voxels represents a single functional network and does not span different functional networks. The single functional network shown in each voxel grouping included in the functional connectivity map is a single function at the level of granularity of the brain function topology used in generating the map. Some functional networks are hierarchical in nature and as such a single brain functional network in one topology may be considered multiple sub-networks in another more granular topology (for example, the sensorimotor network may be considered two functional networks, a sensing functional network and a motor functional network). In this example, each voxel grouping is one of the seven brain functional networks described above. However, in other examples, the voxel groupings can be associated with other brain functional networks not listed or described herein.

Figure 2:
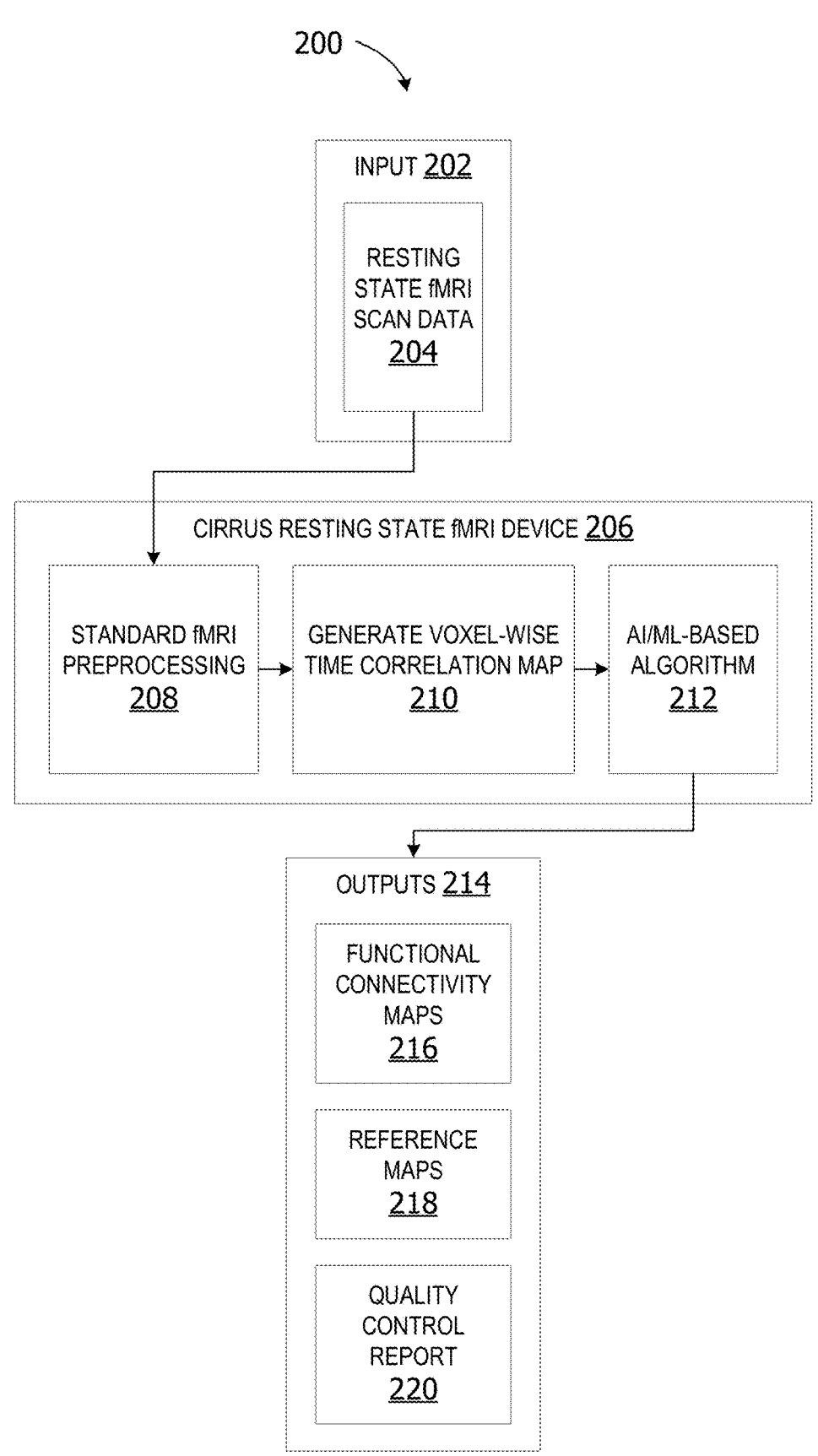
FIG. 2 is an exemplary block diagram illustrating a process for mapping functionally related brain regions on a structural MRI of a subject.

FIG. 2 is an exemplary block diagram of a system 200 such as the system 100 in FIG. 1, simplified to illustrate process flow for mapping functionally related brain regions on a structural MRI of a subject. As shown, the system 200 receives, as device input 202, an MRI data set for a subject that includes resting-state fMRI scan data 204, as shown and also structural MRI image data for the subject (not shown in FIG. 2). The resting state fMRI scan data captures spontaneous brain activations.

With the input 202, the system 200 performs the following functions: (i) measures the degree of temporal correlation (or in other words, a statistical degree of likeness) between different magnetic resonance ("MR") signals throughout the brain (which, given the "resting-state" of the patient during the MRI scan, reveals information regarding the patient's spontaneous brain activations), and compiles those measures in a "voxel-wise time correlation map"; and (ii) based on that correlation map, assigns each voxel of the brain to one (or none) of seven defined brain networks in the seven-network topology upon which the Cirrus device is based (discussed below), thereby generating a set of functional connectivity maps, one for each network in the topology used by the system 200. The seven defined brain networks are separably identifiable across a broad population of patients and are well-understood in the field. The system 200 also generates a corresponding set of seven reference maps, each map comprising population-averaged locations falling within each network overlaid on a structural image of the subject (or a reference structural image), as well as a quality control report.

In more detail and referring to FIG. 2, the resting state fMRI device 206 of system 200 first performs standard fMRI processing 208. Some standard fMRI preprocessing 208 functions are: (i) address scan artifact; (ii) address noise including from patient motion; and (iii) transform the acquired MR data into a normalized brain Atlas space so spatial locations of patient data being processed are comparable to spatial locations used in the Cirrus Device algorithm design. Further detail on preprocessing is discussed below. After all preprocessing is complete, the rs-fMRI data includes, for each voxel of the brain, a time-series set of magnetic resonance (MR) signal samples over the fMRI scan time (for example, 12 minutes in a case where the scan session includes two scans that are six minutes each and are performed back to back), although excluding samples at times where preprocessing determines there was excessive head motion. Given the resting state of the patient during acquisition of the rs-fMRI data, the fMRI scan data reveals information about when spontaneous brain activations have occurred at location of the brain over the time course of the scan session.

Next at block 210, the system 200 generates, from preprocessed rs-fMRI scan data, a voxel-wise time correlation map. A voxel-wise time correlation map provides a brain-wide picture of how the MR signal at one voxel of the brain correlates in time with MR signals at other voxels throughout the brain. In some examples, the system generates a matrix of correlation values of MR signals at each brain voxel versus every other voxel.

For each pair of voxels throughout the brain, the system 200 calculates, for example, a standard Pearson product-moment correlation coefficient for the MR signal at one voxel compared to the MR signal at the second voxel, which yields a single scalar value representing a measure of strength in linear association between the two MR signals. The Cirrus Device does that calculation for all the voxel pairs throughout the brain. As such, the voxel-wise correlation map provides a picture of how the MR signal at each voxel of the brain correlates with all of the other MR signals throughout the brain.

Next at block 212, network assignment is performed. The network assignment function, which in this example includes a nonadaptive AI/machine learning based algorithm component, generates a set of seven functional connectivity maps (one for each defined network), by assigning, based on the voxel-wise correlation map, each brain voxel to one (or none) of seven defined networks. The AI/ML based algorithm component may use, for example, a "perceptron" neural network structure, which is a well-known neural network structure for classifiers that use supervised machine learning. In other words, the AI/ML-based algorithm uses correlation maps to assign each voxel to one (or none) of 7 separable networks.

The data received for processing at block 210, as mentioned above, is the voxel-wise correlation map, which as mentioned, includes brain-wide correlations. The AI/ML algorithm component included in block 212, consistent with how it was trained (discussed below), evaluates network assignment for a voxel based on its brain-wide correlation map, based upon how the MR signal at that particular voxel correlates in time with MR signals throughout the brain. The AI/ML algorithm component, in this example, is a supervised classifier that is well suited to perform "pattern matching" for each voxel's brain-wide correlation map.

Specifically, the system 200 evaluates each voxel's brain-wide correlation map to group voxels into a standardized set of networks based on the global pattern. This global network organization that informs the assignment of a particular voxel to a network provides robustness in brain mapping. Spontaneous brain activations represented in MR signals not only have known time correlation within networks, but also have known time relationships to other networks elsewhere in the brain. Thus, each individual subject, both normally and due to disease (e.g., brain tumor), will have local variations in the anatomic location of a given network. The global pattern however will remain largely unchanged. It is this feature of pattern matching performed by the AI/ML algorithm component using the global pattern of time correlation based functional connectivity that makes the system 200 powerful in its ability to correctly attribute membership to a given network despite individual patient and disease induced variability.

For example, in situations of shifted anatomy (due to the presence of a tumor), the system 200 is able to assign voxels correctly despite a shift due to local mass effect (and the company has examples demonstrating this), given the network assignment factors in the entire organization of MR signals throughout the brain (including in non-shifted locations).

A common RSN mapping approach is to search for activity which correlates with activity at known reference locations or "seeds." A seed is a small (e.g., 0.52 cc) spherical region known to be associated with a particular function in healthy people. Multiple seeds are often used together to avoid spurious correlations. For example, by measuring overall correlation with a constellation of 30 visual seeds, one can identify the visual network.

Referring to the Table below, the system 200 in this example uses a topology of seven well-understood brain networks. This seven-network topology is consistent with topology-defining efforts in the field of resting-state fMRI research that converged upon a standardized set of networks at the macro-scale level of brain network organization.

| Resting State Network | Expanded Acronym | Number of Reference "Seeds" |
|---|---|---|
| DAN | Dorsal Attention Network | 28 |
| VAN | Ventral Attention Network | 15 |
| SMN | Sensori-Motor Network | 39 |
| VIS | Visual Network | 30 |
| FPC | Fronto-Parietal Control Network | 12 |
| LAN | Language Network | 13 |
| DMN | Default Mode Network | 32 |
| | | Total = 169 |

As shown in the Table above, each of the seven networks has a separate set of defined reference "seed" locations. The seven sets of reference "seeds" may be, for example, population-averaged locations that fall within, and are in essence central locations of, the seven respective networks. A total of 169 "seeds" are defined for the seven networks in total, with the DAN having 28, VAN having 15, etc. The reference "seeds" were also used in the AI/ML algorithm training as discussed below and are made available to users in separate reference map outputs to aid in the understanding and interpretation of functional connectivity map outputs for an individual patient.

Supervised training may be used in the training of the AI/ML algorithm component involved in making network assignments. An appropriate number of rs-fMRI datasets from healthy patients may be used in the supervised machine learning training process. For training, each rs-fMRI dataset may first be preprocessed, and a voxel-wise correlation map was generated. Only correlation coefficient data for the 169 reference "seeds" vis-à-vis all brain gray matter may be used, in one example, in training. That means, for example, there are 169 training datasets for each patient rs-fMRI dataset. Specifically, each training dataset may consist of a subset of the voxel-wise correlation map relating to just one voxel corresponding to one of the 169 "seed" locations. As such, the subset correlation map for a particular "seed" location included all calculated correlation coefficients comparing the MR signal at the "seed" location versus all other voxels throughout the brain's gray matter. In other words, this correlation map subset for a "seed" location provided a brain-wide view of MR signal correlation from the perspective of the "seed" location. For supervision, each training dataset (for one "seed" location in one patient dataset) was given an "a priori" network assignment based upon the network to which the "seed" belongs. This training process generates the "weights" for the Cirrus perceptron neural network algorithm that may then be applied during use of the algorithm. In some embodiments, the neural network algorithm may be nonadaptive, in that the weights are set during a design phase of the software-based system. In other embodiments, the neural network is adaptive and is updated periodically or continuously during operation of the system.

The network assignment component 212, including the AI/ML algorithm component, operates to make network assignments to generate output 214 including seven "functional connectivity" maps 216, one for each of the seven defined networks. Specifically, the AI/ML algorithm component first generates, for each voxel, seven values each representing a degree of confidence that the voxel is a member of each of the seven networks. Then, for each voxel, if the highest confidence value is above a set threshold (set at a 97% confidence level), an assignment is made to a network corresponding to the network having the highest confidence value.

In addition, the system 200 also generates a corresponding set of seven reference maps 218, one per brain function (population averaged data). Each map comprising population-averaged locations falling within each network overlaid on a structural image of the subject (or a reference structural image), as well as a quality control report 220. The reference locations define points within a normalized brain atlas that are consistently identified at a population level as being members of the functional network for the seven brain functions of the brain function topology used by the system 200. In one example, the reference locations are shown in reference location maps as 5 mm spheres. And as discussed, these population-level reference locations can be used to define the machine-learning training datasets used to train the AI/ML algorithm component.

The machine-learning based algorithm is tuned from the training data (e.g., the reference locations) to generate an output conforming to a readily understood brain function topology. The addition of the reference information output assists trained radiologists in evaluating the functional connectivity maps generated by the system 100, 200. Maps of the reference location information are a valuable complement to a radiologist's clinical training and knowledge for the interpretation and evaluation of the functional connectivity maps.

Figure 3:
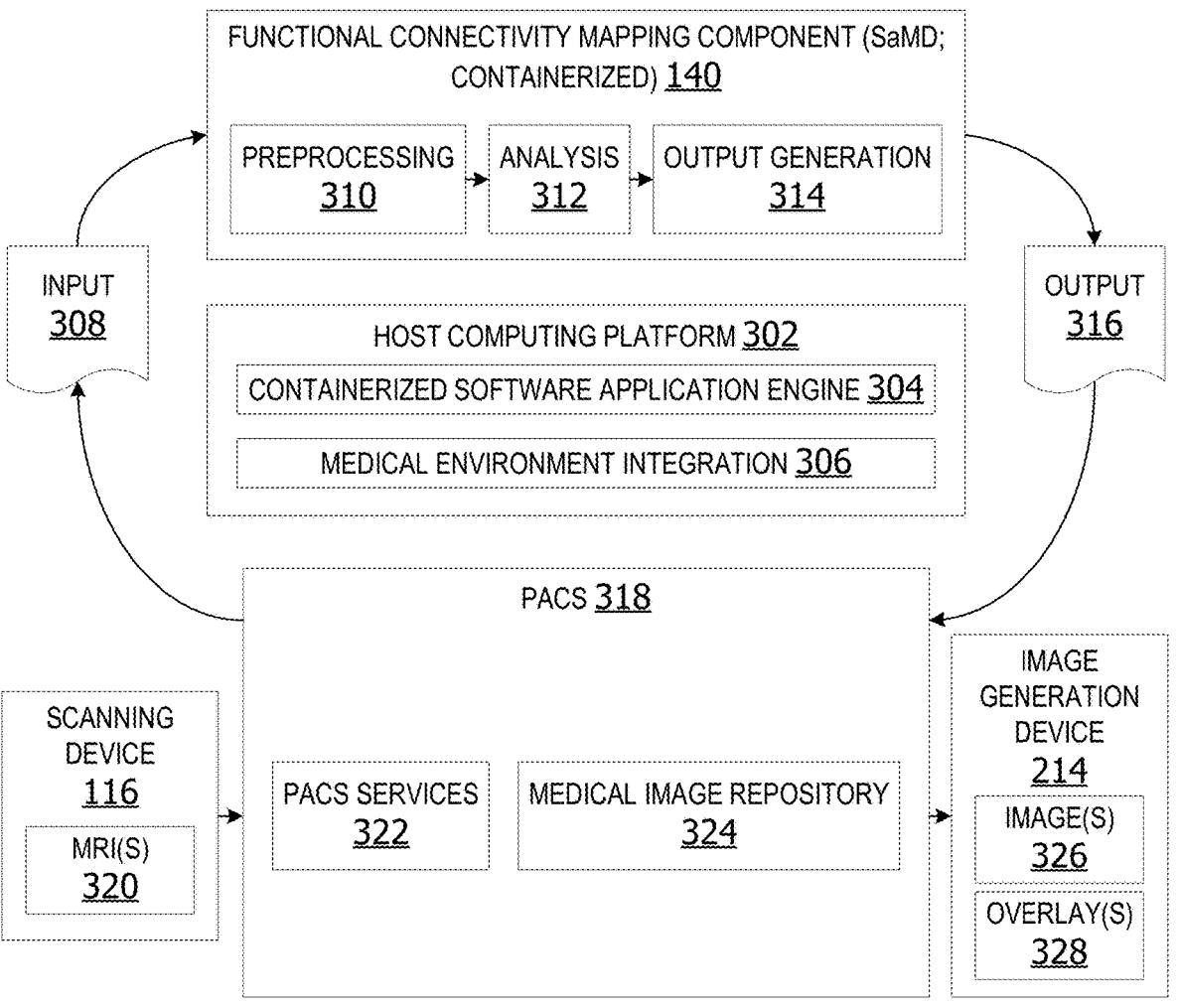
FIG. 3 is an exemplary block diagram illustrating a system for processing MRI datasets to generate functional connectivity maps and corresponding reference maps

Turning now to FIG. 3, an exemplary block diagram illustrating a system for processing MRI datasets to generate, from a subject's MRI dataset that includes rs-fMRI data, functional connectivity maps and corresponding reference maps is shown. In this example, the functional connectivity mapping component 140 is a software as medical device (SaMD) designed to be deployed within a radiology information technology (IT) ecosystem that includes a host computing platform 302 (also referred to as a host system) and a picture archiving and communication system (PACS) 318.

The functional connectivity processing component 140 processes datasets of MRI 320 in standard Digital Imaging and Communications in Medicine (DICOM®) format generated by the scanning device 116. In operation, the functional connectivity processing component 140 performs three main functions: preprocessing raw input MRI data 308; conducting a functional connectivity analysis 312 on the preprocessed MRI data 312; and output generation 314. In this example, the output 316 generated includes DICOM®-formatted brain maps and a PDF-formatted quality control (QC) report. The details of these three main functions and the outputs generated by the functional connectivity processing component 140 are described below.

The functional connectivity processing component 140, in this example, runs on a host computing platform 302. Specifically, in this example, the functional connectivity processing component is a fully "containerized" software application designed to be executed using a containerized software application engine 304 residing on a host computing platform 302 (which forms a virtual operating system to execute the functional connectivity processing component operations), as shown in FIG. 3. The fully containerized design of enables it to be run on host computing platforms having an operating environments (Linux, Microsoft Windows, and MacOS), with the host computing platform having installed thereon a containerized software application engine 304.

The functional connectivity processing component 140 does not include display capability for users to view the generated outputs 316. Instead, the DICOM®-formatted brain maps may be viewed using software (external of the computing device 102) with DICOM® image viewing capability associated with the image generation device 214. PDF-formatted Quality Control (QC) Reports generated by the computing device 102 may be viewed and/or printed using software (external of the functional connectivity processing component 140) with PDF viewing and printing capability. The host computing platform and/or the PACS may have such DICOM® and/or PDF viewing capabilities, as well as features designed to enable a radiologist to visualize and annotate DICOM® formatted images such as the functional connectivity processing component created brain maps. In some examples, the image generation device 214 includes software for displaying, generating, or otherwise presenting the fMRI image(s) 326 with overlay(s) 328 generated by the mapping generated for viewing by a human user.

In this example, the functional connectivity processing component has no impact on image generating devices and does not provide automated diagnostic interpretation capabilities such as computer assisted diagnosis (CAD). All output image data are to be evaluated and interpreted by trained medical professionals.

The functional connectivity processing component in some examples is designed to be deployed within a radiology information technology (IT) ecosystem, which includes a host computing platform (external of the functional connectivity processing component 140) and a picture archiving and communication system (PACS) (also external of the functional connectivity processing component 140).

Given the fully containerized design, a host computing platform has installed thereon a containerized software application engine that launches and operates the functional connectivity processing component in a virtual container. In this example, the host computing platform includes Docker software v20+, developed by Docker, Inc., as its containerized software application engine. The host system may use any operating environments (Linux, Microsoft Windows, and MacOS). The host computing platform optionally includes medical workflow integration, security and access control, and data privacy tools. The host computing system may have DICOM® and/or PDF viewing capabilities, as well as features designed to enable a radiologist to visualize and annotate DICOM® formatted images such as the generated brain maps.

The PACS 318 provides a standard repository for DICOM® formatted image files input to the functional connectivity processing component 140 for processing, as well as the DICOM® formatted image files output by the functional connectivity processing component 140. The PACS may include PACS software service tools with DICOM® and/or PDF viewing capabilities, as well as features designed to enable a radiologist to visualize and annotate DICOM® formatted images such as the functional connectivity processing component 140 generated brain maps.

In other examples, the containerized functional connectivity processing component is operated within a radiology information technology (IT) infrastructure comprised of a host computing platform that executes the functional connectivity processing component 140 software instructions, and the PACS, that provides electronic storage for the electronic input and output files received and generated by the functional connectivity processing component 140. In this example, the functional connectivity processing component 140 selects and receives an input MRI data set; performs three main functions upon the input MRI data set, which are preprocessing the input MRI data, conducting functional connectivity analysis on the preprocessed MRI data, and generating three types of outputs; and outputs the generated electronic files.

In other examples, a trained radiology user launches and operates the functional connectivity processing component 140. Specifically, the user uses a host computing platform to launch the functional connectivity processing component 140 and to select and access, from within the PACS, an individual subject's MRI data set for the functional connectivity processing component 140 to process.

MRI data sets are stored, conventionally, in a PACS, where they may be accessed for processing by the functional connectivity processing component 140. The functional connectivity processing component 140 converts DICOM images to the standard scientific NIfTI format before translation to the 4 dfp format for preprocessing and analysis.

In some examples, the input MRI data set for the subject includes: (1) structural MRI data (e.g., T1-Weighted MR data) of the subject's head and brain; and (2) rs-fMRI data (e.g., T2*-Weighted BOLD MR data) of the subject's brain, both in standard DICOM® format. The input MRI data set are acquired outside of (before) the functional connectivity processing component's operation, using 3 Tesla (3T) MRI scanning equipment. The structural MRI data and rs-fMRI data may be acquired during the same MRI scan session. Anatomical imaging data are typically from a single sagittal T1-weighted (T1W) magnetization prepared rapid gradient echo (MP-RAGE) scan.

The rs-fMRI data are acquired using a BOLD contrast sensitive gradient echo echo-planar sequence (typical parameters are 4 mm slice thickness, 90° flip angle, 2330 ms TR, and 27 ms TE), with the subject lying in the MRI scanner in a state of rest, in two separate six-minute scans conducted in the same imaging session, back-to-back, with a brief time interval between. This generates, typically, 160 frames of fMRI data for each six-minute run, where a frame is a single scan volume.

The first main function performed by the functional connectivity processing component is preprocessing the raw input MRI data, following commonly used MRI and fMRI data processing practice. Raw MRI and fMRI data contains noise and artifacts that can be addressed using established pre-processing methods before analysis. The functional connectivity processing component includes compensation for slice-dependent time shifts, elimination of systematic odd-even slice intensity differences due to interleaved acquisition, and rigid body correction of head movement within and across runs. Additionally, the functional connectivity processing component transforms MR data to standard atlas space through composition of affine transforms that connect (register) fMRI volumes with the structural fMRI images.

The functional connectivity processing component further performs functional connectivity analysis of the preprocessed data. In some examples, the functional connectivity analysis includes two main steps. First, a voxel-wise correlation map is generated from the preprocessed rs-fMRI data. The voxel-wise correlation map identifies, for each voxel of the brain, a measure of the degree of time correlation between the spontaneous brain activations at a particular voxel of the brain and the spontaneous brain activations at every grey matter voxel of the brain (with standard masks being used to isolate the brain voxels and grey matter voxels). Second, a machine-learning algorithm is applied to the voxel-wise correlation map to calculate a degree of confidence that each brain voxel belongs to each of the seven defined brain functions of the brain function topology used in the functional connectivity processing component (e.g., the well-defined brain functions of DAN, VAN, SMN, VIS, FPC, LAN, and DMN, as set forth in Section II.C). As discussed previously in Section II.C, the brain function topology used in the functional connectivity processing component delineates seven major brain functions that may consistently be found in a broad population of human subjects from an evaluation of time correlations in spontaneous brain activation data.

The functional connectivity processing component's machine-learning algorithm is also sometimes referred to as a multi-layer perceptron (MLP). The functional connectivity processing component's MLP consists of three layers: one input layer, one hidden layer, and one output layer, each consisting of nodes fully connecting to the next layer (all-to-all feed-forward). The MLP was developed using supervised learning. This technique involves the feeding of classified data inputs (e.g., training data) into the MLP and the iterative adjustment of layer connection weights to minimize the overall error rate of the MLP. The final connection weight files produced by training the MLP are used by the functional connectivity processing component to produce a probability for the classification of each voxel to a certain brain function of the seven brain functions of the functional connectivity processing component topology (DAN, VAN, SMN, VIS, FPC, LAN, and DMN).

Generally, the training of the algorithm may use sets of population-averaged reference, or "seed," locations for the seven top-level RSNs. There may be a set of seed locations for each network, derived from a meta-analysis of task-based fMRI literature wherein task-study comparisons were used to identify brain locations (seeds) with high likelihood of activation upon task performance. The reference, or seed, locations may be defined in stereotactic space within a standard Atlas structure. The initial seed locations may be refined to produce final seed locations used in algorithm training; this refinement process may be conducted to ensure that the RSNs of the topology are maximally separable.

Training data may be generated by first obtaining resting-state fMRI scan data from a number of healthy subjects. Healthy subjects may be chosen so that there is a strong degree of confidence that the population-averaged seed locations for the seven networks fall within the same corresponding networks for all subjects. Additionally, selecting only healthy patients may prevent the AI/ML algorithm from learning patterns which are lesion-specific or cognitive-deficit specific and therefore not replicable across majority of patients. Each subject dataset may undergo the same standard fMRI preprocessing as used in the device. Then, correlation coefficients may be calculated between the MR signals in each seed location (e.g., 175 such locations per subject) and the MR signals in each grey matter voxel of the brain (~31K voxels per subject) using the Pearson product-moment correlation calculation. The resulting maps hold the brain-wide patterns of functional connectivity from the perspective of each seed location. Given that the process used to select seeds brought high confidence in each seed's larger membership score for a class representing a higher certainty that the input is of that class, and a lesser membership score representing a higher certainty that the input is not of that class. For each training instance, the output labels, or desired membership score output values, may be 1 for the class matching the seed's RSN identity and 0 for all other classes. Using the output labels (desired outputs) and membership scores generated by the MLP, error is calculated as the difference between the output label value and membership score for a class. Using all error values (8 classes×the number of training instances), root mean square error may be calculated to reflect MLP performance on the entirety of the training data with one metric. Then, the well-known backpropagation method may be used to adjust the MLP weights with the goal of minimizing root mean square error. This process of generating output for the input data, calculating error, and performing backpropagation may be completed for tens of thousands of iterations to generate the fully trained model.

In more detail, the training datasets may in one example consist of the data shown in the table below:

| Characteristics of the Training, Test and Validation datasets. | | | | |
|---|---|---|---|---|
| Dataset | Training | Optimization | Validation 1 | Validation 2[§] |
| Number of Subjects | 21 (7M + 14 F) | 17 (8M + 9F) | 10 (4M + 6F) | 692 (305M + 387F) |
| Age in years | 27.6 (23-35) | 23.1 (18-27) | 23.3 ± 3 (SD) | 21.4 ± 2.4 (SD) |
| Scanner | Allegra | Allegra | Allegra | Tim Trio |
| Acquisition voxel size | (4 mm)³ | (4 mm)³ | (4 mm)³ | (3 mm)³ |
| Flip angle | 90° | 90° | 90° | 85° |
| Repetition Time (sec) | 2.16 | 2.16 | 3.03 * | 3.00 |
| Number of frames | 128 × 6 runs | 194 × 4 runs | 110 × 9 runs | 124 × 2 runs |
| Citation | (Lee et al., 2012) | (Fox and Raichle, 2007) | (Fox et al., 2005) | (Yeo et al., 2011) |

* Validation data set 1 included a one second pause between frames to accommodate simultaneous electroencephalography (EEG) recording.
[§]Validation data set 2 was acquired at Harvard-MGH by the Bram Genomics Superstruct Project.

RSN identity on a per-patient basis, the calculated seed correlation maps exemplified the brain-wide patterns of functional connectivity associated with the seed's respective RSN. As such, the algorithm training process enables the device MLP component to learn the associations between brain-wide functional connectivity patterns and an RSN identity label.

Algorithm training may consist of first propagating training instances (a single training instance being one PCA-reduced seed correlation map) through the MLP to generate 8 membership score outputs (one for each of seven RSNs, plus one for the nuisance class) per training instance. Membership score may be any value between 0 and 1, with a In this example, 740 input data sets were produced using seven sets of population-level reference locations (also called "regions of interest," or "ROIs") for each of the seven brain functions of the topology (DAN, VAN, SMN, VIS, FPC, LAN, and DMN), as set forth in the table below. See Hacker et al., Resting state network estimation in individual subjects (2013).

These population-level reference locations are also referred to as "seed locations" or seed ROIs, owing to these stereotactic locations serving as the starting points (that is, comparison points) in the time correlation analysis to generate the data sets used in the development of the functional connectivity processing component algorithm.

| Studies of functional co-activation used to generate seed ROIs. | | | | | |
|---|---|---|---|---|---|
| RSN | Expanded acronym | Citation | Task paradigm | Task contrast | Final seed ROIs |
| DAN | Dorsal Attention Network | (Shulman et al., 2009; Tosoni et al., 2012) | Rapid Serial Visual Presentation (RSVP) | Cue Type × Time | 28 |
| | | (Shulman et al., 2009; Tosoni et al., 2012) | Rapid Serial Visual Presentation (RSVP) | Cue Location × Cue Type × Time | |
| | | (Astafiev et al., 2004; Corbetta et al., 2000; Kincade et al., 2005) | Posner Cueing Task | Time | |

| Studies of functional co-activation used to generate seed ROIs. | | | | | |
|---|---|---|---|---|---|
| RSN | Expanded acronym | Citation | Task paradigm | Task contrast | Final seed ROIs |
| VAN | Ventral Attention Network | (Astafiev et al., 2004; Corbetta et al., 2000; Kincade et al., 2005) | Posner Cueing Task | Invalid vs. Valid | 15 |
|  |  | (Dosenbach et al., 2007) | 10 different cognitive control tasks* | Graph theoretic analysis |  |
| SMN | Sensori-Motor Network | (Corbetta et al., 2000; Kincade et al., 2005) | Posner Cueing Task | Motor response | 39 |
|  |  | (Petacchi et al., 2005) | Various auditory stimuli | Stimulation vs. Control |  |
| VIS | Visual network | (Sylvester et al., 2008; Sylvester et al., 2007, 2009) | Visual Localizer | Discrete visual stimuli | 30 |
| FPC | Fronto-Parietal Control network | (Dosenbach et al., 2007) | 10 different cognitive control tasks* | Graph theoretic analysis | 12 |
| LAN | Language network | (Sestieri et al., 2011; Sestieri et al., 2010) | Perceptual vs. Episodic Memory Search Paradigm | Sentence reading | 13 |
| DMN | Default Mode Network | (Sestieri et al., 2011; Sestieri et al., 2010) | Perceptual vs. Episodic Memory Search Paradigm | Memory retrieval | 32 |

*Regions reported by Dosenbach and colleagues (2007) were themselves the result of a meta-analysis.

Each of the 740 input datasets consists of a voxel-wise Pearson-product moment correlation coefficient map produced from the subject's preprocessed rs-fMRI data (spontaneous brain activations) and accompanying brain function output labels.

The training input datasets are comprised of correlation maps calculated between (1) the frame-wise average value of voxels within a single seed ROI that is associated with a specific functional group and (2) all grey matter voxels of the subject's brain. Accompanying the input correlation map is an output label matrix that has a value of 1 for the functional group to which the ROI belongs and a value of 0 for all other functional groups (including one nuisance class). The nuisance class portion of training data in this example is constructed with 6 ROIs located at population-level average cerebrospinal fluid regions in the brain. The nuisance class represents estimates for voxels to be of non-interest for functional connectivity mapping, given that correlation patterns in cerebrospinal fluid regions do not indicate those voxels being associated with a particular brain function.

One input correlation map and output label pair was generated for each of 175 ROIs (169 ROIs associated with the 7 functional groups in total, and 6 ROIs used for the nuisance class), for each of the subjects in the training dataset. During training, the MLP outputs probability estimates for each input correlation map's belonging to each of the 8 classes (7 functional groups or the nuisance class), compares these output probabilities to the discrete output labels provided (value of 1 for the correct class, value of 0 for the other classes), and iteratively reduces the error by adjusting connection weights.

In verification, the fully trained MLP was applied at the whole-brain level. The verification input datasets are comprised of correlation maps calculated between each brain voxel and each grey matter voxel. Accompanying the input correlation map is an output label matrix for each ROI voxel. This output label matrix has a value of 1 for the functional group to which the ROI voxel belongs and a value of 0 for all other functional groups (including one nuisance class). In this example, output labels were not used in verification to further adjust connection weights, but to compute RMS error to assess the performance of the MLP.

The functional connectivity processing component performs three output generation routines to generate three types of outputs for display and evaluation outside of the functional connectivity processing component. The three types of outputs generated by the functional connectivity processing component are as follows: (1) a PDF-formatted quality control (QC) report; (2) a set of seven DICOM®-formatted functional connectivity (FC) maps, each overlaid upon the subject's structural brain image; and (3) a set of seven DICOM®-formatted population-level brain function reference location maps (one map for each predefined functional network: DAN, VAN, SMN, VIS, FPC, LAN, and DMN), each overlaid upon the subject's structural brain image.

The first type of output generated by the functional connectivity processing component is a PDF-formatted quality control (QC) report showing relevant quality parameters and charts for a trained radiology user to evaluate the quality of the rs-fMRI scan data and the success of data processing. The QC report ensures the reliability of the functional connectivity processing component's functional connectivity maps. This report provides a concise way for trained users to review the functional connectivity processing component's performance for the purpose of identifying any issues with the functional connectivity processing component's performance, for example, those that originate from excessive movement in input MRI scans.

While the design of the QC report may include the following information: (1) information that clearly identifies the document as a Quality Control Report; (2) information that clearly identifies the functional connectivity processing component run for which the Quality Control Report is produced; (3) a warning about the sensitivity of protected health information (PHI); (4) MRI input data provenance including subject names for each scan shown as clearly as possible, given possible anonymization of MRI data; (5) application version and last update date/time; (6) reference materials for evaluating QC report contents; and, (7) a summary of key information that indicates the mapping application run performance. The Quality Control Report is clearly labelled, so that the report is easily interpreted by trained users. The content included in the Quality Control Report is presented in such a way that errors are apparent to trained users, so that users reliably and repeatably reject faulty output.

The QC report is reviewed by a trained radiology user as part of the mandatory workflow. The radiology users may be healthcare professionals associated with the imaging centers at which the functional connectivity processing component is deployed.

The second type of output generated by the functional connectivity processing component is a set of seven functional connectivity maps in standard DICOM® format. Each FC map is a separate grouping of functionally connected brain volume elements (voxels) in the individual subject's brain. Voxels grouped together are functionally connected because spontaneous brain activations at each voxel are highly time correlated with spontaneous brain activations at all other voxels in the same grouping. The degree of time correlation that the functional connectivity processing component requires for inclusion in a grouping is determined by the functional connectivity processing component output requirement that the machine-learning algorithm's confidence that the voxel is included in the grouping be at least 0.97 (on a 1.00 scale). The seven output voxel groupings correspond to the seven primary brain functions used in the functional connectivity processing component include: DAN, VAN, SMN, VIS, FPC, LAN, and DMN. However, the brain functions for each of the voxel groupings (FC maps) are not labeled in the functional connectivity processing component functional connectivity map output. Accordingly, the functional connectivity processing component output reflects a tool-based "measurement" of time-correlation of spontaneous brain activations at different brain locations, and groups together those voxels of a subject's brain whose spontaneous activations are highly time correlated.

In some examples, the functional connectivity processing component includes a supervised machine-learning algorithm, referred to as a multi-layer perceptron (MLP), which is trained and optimized according to standard machine-learning training methodologies using fMRI data sets to create an algorithm that is used to map the predefined resting state networks (RSN)—e.g., functionally connected voxel groupings—in individuals. The primary RSN topology used in the functional connectivity processing component may be determined in part, based upon a meta-analysis of task-based fMRI studies. In some examples, the RSNs includes seven primary brain functions, which are as follows: (1) dorsal attention network (DAN), (2) ventral attention network (VAN), (3) sensorimotor network (SMN), (4) vision network (VIS), (5) frontoparietal control network (FPC), (6) language network (LAN), and (7) default mode network (DMN), as discussed in FIG. 16 through FIGS. 22A-22G below. The system's functional connectivity (RSN) maps can be verified with additional fMRI data sets.

In one example, the system's maps may be directly compared with outputs from two alternative software-based RSN mapping techniques, namely, dual regression (DR) and linear discriminant analysis (LDA). The maps generated by the functional connectivity processing component can be shown to be more spatially specific RSN maps than either alternative for higher mapping performance.

Figure 4:
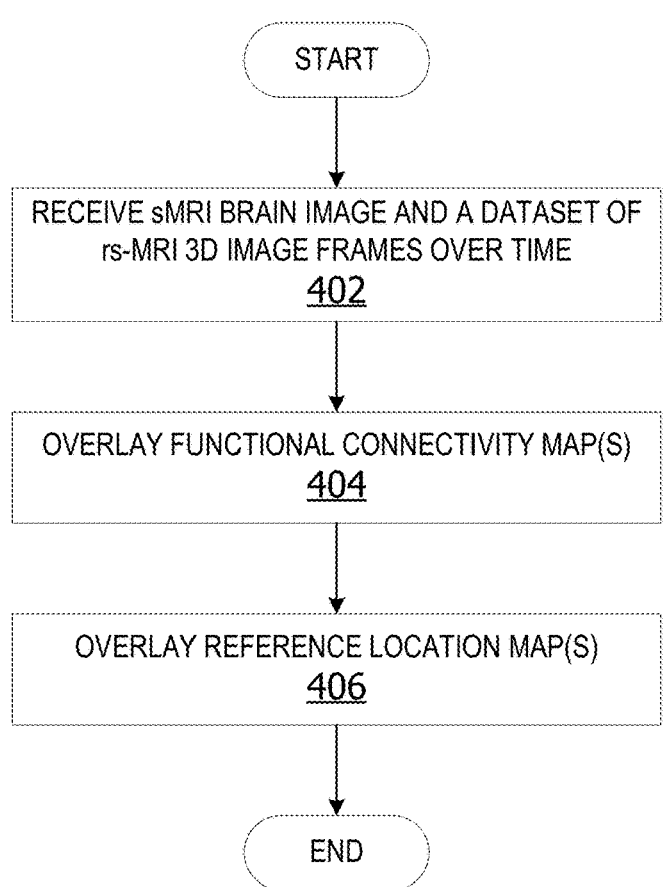
FIG. 4 is an exemplary flow chart illustrating operation of the computing device to generate one or more functional connectivity map(s) and/or one or more reference location map(s).
Figure 5:
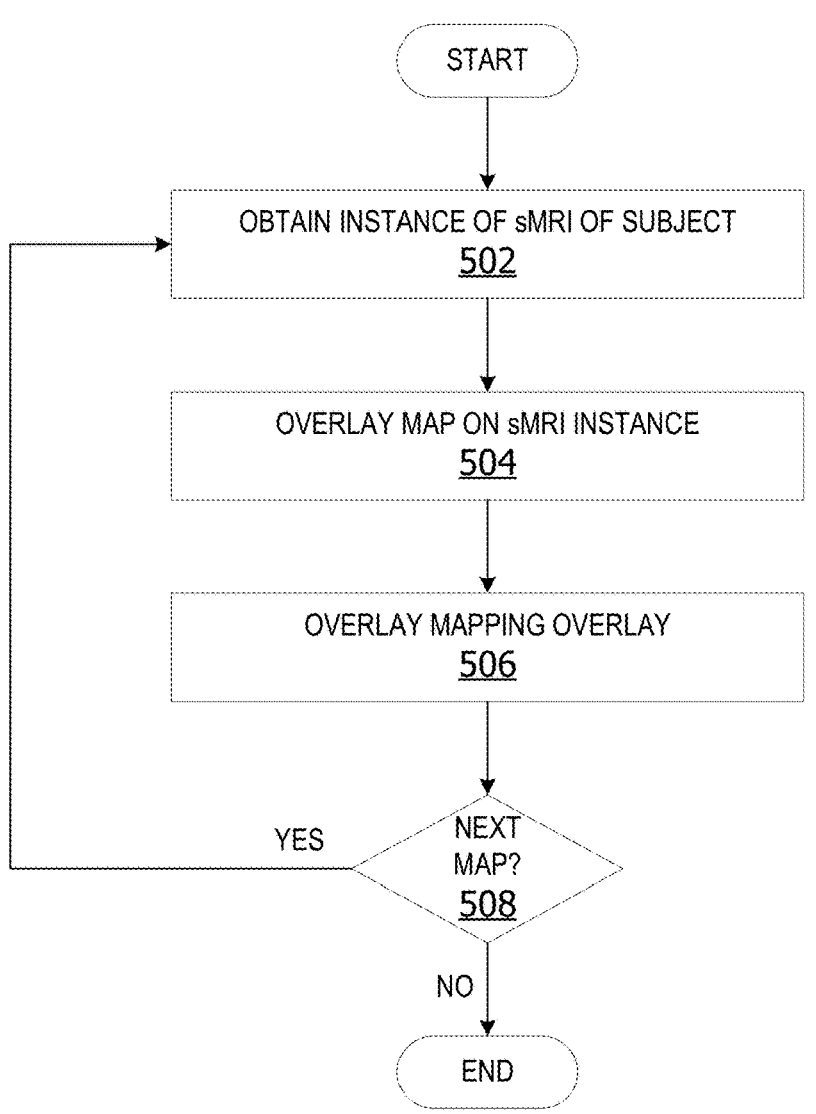
FIG. 5 is an exemplary flow chart illustrating operation of the computing device to generate a plurality of brain functional connectivity maps and/or reference location maps.

Referring now to FIG. 4, an exemplary flow chart illustrating operation of the computing device to generate one or more functional connectivity map(s) and/or one or more reference location map(s) is depicted. The process shown in FIG. 5 is performed by a functional connectivity processing component, executing on a computing device, such as the computing device 102 or the user device 120 in FIG. 1.

The functional connectivity processing component receives a structural MRI brain image of a subject and a dataset of rs-MRI 3D image frames of the subject brain over time at 402. The structural MRI brain image may be an image of an individual subject or a standardized subject. The functional connectivity processing component combines one or more functional connectivity map(s) on the structural MRI brain image at 404. The functional connectivity processing component combines the structural MRI brain image with one or more reference location map(s) at 406. A reference location map may be overlaid on a different instance of the structural MRI brain image than the instance of the structural MRI brain image on which the functional connectivity map is overlaid. In other examples, the reference location map and the functional connectivity map are overlaid on the same structural MRI brain image of the subject. The process terminates thereafter.

While the operations illustrated in FIG. 4 are performed by a computing device, aspects of the disclosure contemplate performance of the operations by other entities. In a non-limiting example, a cloud service performs one or more of the operations. In another example, one or more computer-readable storage media storing computer-readable instructions may execute to cause at least one processor to implement the operations illustrated in FIG. 4.

In some examples, computer executable instructions are provided using any computer-readable media that are accessible by a computing apparatus. Computer-readable media include, for example, computer storage media such as memory and communications media. Computer storage media include volatile and non-volatile, removable, and non-removable media implemented in any method or technology for storage of information such as computer readable instructions, data structures, program modules or the like. Computer storage media include, but are not limited to, Random Access Memory (RAM), Read-Only Memory (ROM), Erasable Programmable Read-Only Memory (EPROM), Electrically Erasable Programmable Read-Only Memory (EEPROM), persistent memory, phase change memory, flash memory or other memory technology, Compact Disk Read-Only Memory (CD-ROM), digital versatile disks (DVD) or other optical storage, magnetic cassettes, magnetic tape, magnetic disk storage, shingled disk storage or other magnetic storage devices, or any other non-transmission medium that can be used to store information for access by a computing apparatus. In contrast, communication media may embody computer readable instructions, data structures, program modules, or the like in a modulated data signal, such as a carrier wave, or other transport mechanism. As defined herein, computer storage media do not include communication media. Therefore, a computer storage medium should not be interpreted to be a propagating signal per se. Propagated signals per se are not examples of computer storage media. It will be appreciated by a person skilled in the art, that, in some examples, the storage is distributed or located remotely and accessed via a network or other communication link (e.g., using a communication interface).

FIG. 5 is an exemplary flow chart illustrating operation of the computing device to generate a plurality of brain functional connectivity maps and/or reference location maps. The process shown in FIG. 5 is performed by a functional connectivity processing component, executing on a computing device, such as the computing device 102 or the user device 120 in FIG. 1.

The functional connectivity processing component obtains an instance of a structural MRI of a subject at 502. The subject may be an individual or the subject may be a standardized subject. The functional connectivity processing component overlays the structural MRI instance with a map at 504. The map may be a functional connectivity map or a reference location map. The mapping overlay including the map overlaid on the structural MRI is output at 506. A determination is made whether there is a next map to overlay at 508. If yes, the process iteratively continues overlaying instances of the structural MRI with the one or more map(s) until there are no more functional connectivity maps and/or reference location maps. The process terminates thereafter.

While the operations illustrated in FIG. 5 are performed by a computing device, aspects of the disclosure contemplate performance of the operations by other entities. In a non-limiting example, a cloud service performs one or more of the operations. In another example, one or more computer-readable storage media storing computer-readable instructions may execute to cause at least one processor to implement the operations illustrated in FIG. 5.

Figure 6:
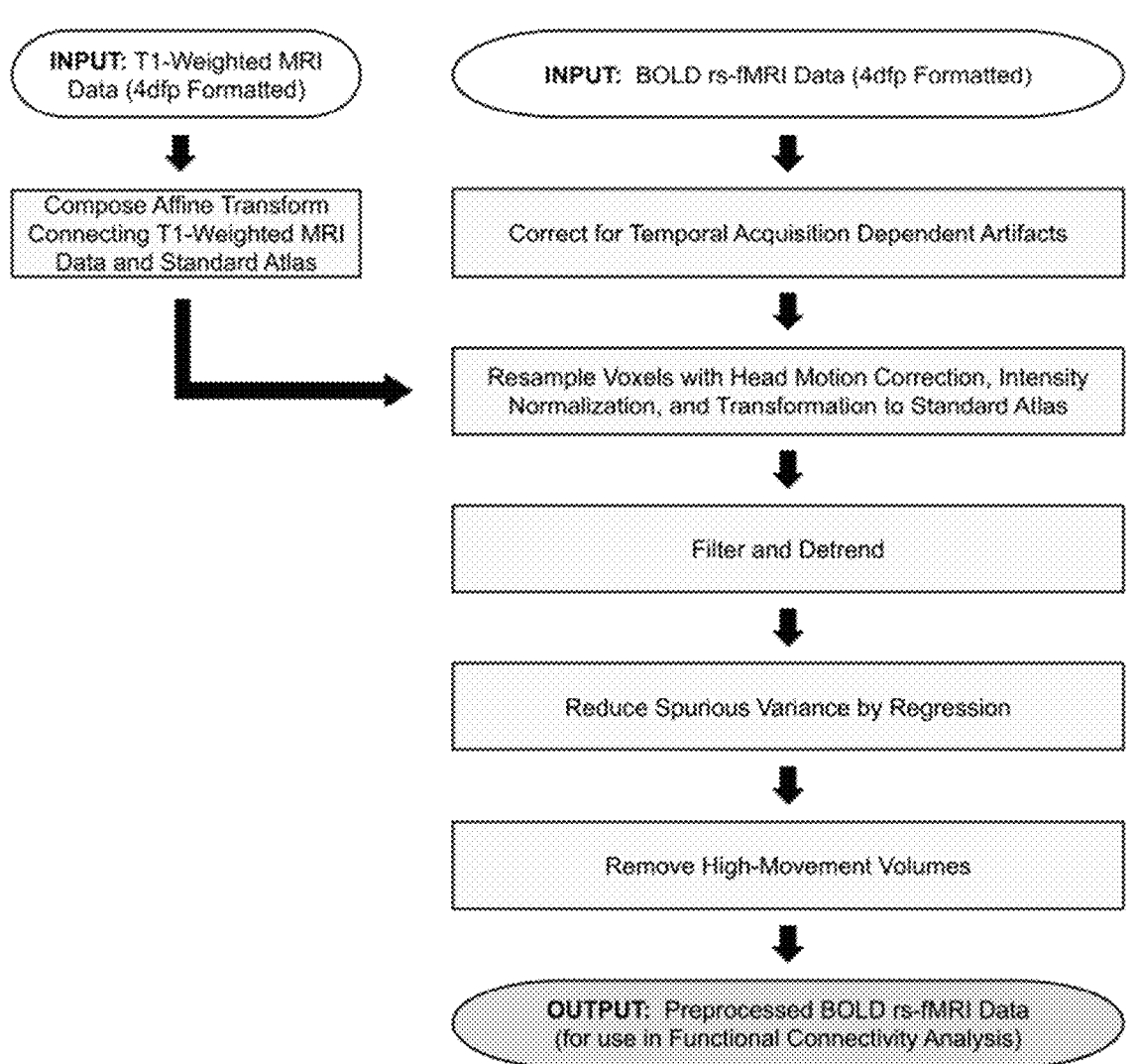
FIG. 6 is an exemplary flow chart illustrating a mapping generation preprocessing pipeline.

FIG. 6 is an exemplary flow chart illustrating a mapping generation preprocessing pipeline, which may be used in preprocessing step 208 in the FIG. 2 method or the preprocessing component 310 in the FIG. 3 system. In this example, the first input to the preprocessing pipeline is the subject's BOLD rs-fMRI data, converted to 4 dfp format. The system corrects for temporal acquisition dependent artifacts. In this step, corrections are made to the BOLD rs-fMRI data for slice-dependent time shifts, as well as slice intensity differences due to interleaved acquisition. Slice-dependent time shifts occur due to slices within a frame being acquired at different times, which may significantly impair fMRI results. Interleaved slice acquisition is performed routinely by fMRI scanners to avoid scan distortion caused by partial excitation of adjacent slices. However, interleaved slice acquisition results in a non-monotonic offset delay between spatially sequential slices since they are not collected in a temporally sequential fashion, which results in slice intensity differences between the interleaved slices. Slice-timing correction and slice intensity correction successfully compensate for these effects and therefore increase the robustness of the data analysis.

T1-weighted MRI data is converted to 4 dfp format. The input to this portion of the preprocessing pipeline is the subject's T1-Weighted MRI data, converted to 4 dfp format. An affine transform is composed that connects the subject's T1-Weighted MRI data to the atlas-space representative target. This involves the use of a 4 mm full-width half-maximum Gaussian blur for spatial smoothing of the T1-Weighted image prior to affine transform composition, as well as the use of brain masking when registering the smoothed T1-Weighted image to the atlas-space representative target.

The system resamples voxels with head motion correction, intensity normalization and transformation to standard atlas. In this step, head motion correction, voxel intensity normalization, and transformation to a standard atlas are performed on the BOLD scans in one resampling step. Head movement is corrected within and across BOLD scans using rigid body correction. The data are intensity scaled to obtain a mode value of 1000 by applying one multiplicative factor to all voxels of all frames within each BOLD scan. Atlas transformation is achieved by composition of an affine transform that connects the subject's BOLD scans to the atlas-space representative target. This is accomplished by first composing an affine transform that connects an average of the subject's BOLD first-frame volumes with the subject's T1-Weighted structural image, then combining this BOLD to T1-Weighted transform with the previously composed T1-Weighted to atlas-space representative target transform (see previous step, "Compose Affine Transform Connecting T1-Weighted MRI Data and Standard Atlas"). Movement correction, voxel intensity normalization, and atlas transformation of the BOLD scans are then conducted in one resampling to 3 mm$^3$ voxels to minimize blur and noise.

To filter and detrend, spatial smoothing is performed using a 6 mm full-width half-maximum Gaussian blur in each direction. Additionally, a voxel-wise removal of linear trends over each BOLD scan is performed, followed by the application of a temporal $2^{nd}$ order low-pass Butterworth filter to retain frequencies <0.1 Hz. This preprocessing step is used to remove fluctuations in BOLD signal which are unlikely to be involved in specific regional correlations.

Spurious variance is reduced by regression. In this step, spurious variance is reduced by regression of nuisance waveforms derived from head motion correction and extraction of the time series from regions of non-interest in white matter and cerebrospinal fluid. Additionally, this step includes regression of the global signal averaged over the whole brain. Since brain voxels are classified based on positive correlation, global signal regression is included in preprocessing as this method is reported to improve the specificity of positive correlations. As in the previous "Filter and Detrend" step, the purpose of regression of nuisance waveforms is to remove fluctuations in BOLD signal which are unlikely to be involved in specific regional correlations.

High-movement volumes are removed. In this step, a temporal masking technique is used to remove BOLD volumes which are contaminated by large head movements and therefore of low data quality. A volume is determined to have excessive head movement and removed if the volume exceeds a limit of quantified voxel-wise intensity change in comparison to the previous timepoint. Various studies have found no deleterious effects upon functional connectivity when discontinuous rs-fMRI data is concatenated and used for functional connectivity analysis.

Bold rs-fMRI data is preprocessed. The output of the preprocessing routines is BOLD rs-fMRI data in the 4 dfp format. For each voxel of the brain, which has been atlas transformed to 3 mm$^3$ voxel space, there exists a BOLD signal intensity value for multiple points in time. The raw rs-fMRI BOLD signal intensity values, from the BOLD inputs, have been adjusted by the preprocessing routines to reduce noise and artifacts prior to the subsequent functional connectivity processing component function, which is Functional Connectivity Analysis.

Additionally, BOLD signal intensity data for certain points in time, meaning entire frames, may be removed from the output data due to the occurrence of large head movements during scan acquisition. This process serves to remove low quality data prior to functional connectivity analysis, and thereby improves the performance of the functional connectivity processing component functional connectivity analysis software function.

FIG. 7 is an exemplary flow chart illustrating functional connectivity analysis. Multiple sets of voxel-wise spontaneous brain activation intensity values are received as input. The input for the functional connectivity analysis is the output of the functional connectivity processing component fMRI Preprocessing Pipeline: Preprocessed BOLD rs-fMRI data, or otherwise put, multiple sets of voxel-wise spontaneous brain activation intensity values.

Voxel-wise correlation map for spontaneous brain activations is generated. The calculation of a correlation mapping for brain voxels serves as the input data for the functional connectivity analysis algorithm. This correlation mapping consists of the calculated Pearson's correlation coefficient value between each brain voxel and each grey matter voxel, where these voxels are isolated through mask application and each grey matter voxel is included in the brain voxel volume. The Pearson's correlation coefficient value for each voxel pair indicates a measure of correlation, or anti-correlation, of the two voxel's spontaneous brain activation intensity values across the BOLD volumetric timeseries.

Voxel-wise correlation map is applied to the MLP algorithm. The functional connectivity MLP input layer consists of the voxel-wise correlation map of spontaneous brain activation intensities across the BOLD volumetric timeseries. The hidden layer is computed using "final" weight matrices determined from MLP training, and a hyperbolic tangent activation function. The output layer is computed using a separate "final" weight matrix determined from MLP training and no activation function. The MLP output is an eight-variable "label matrix" for each brain voxel, where values of the matrix are raw identity scores for class membership, where the 8 variable classes correspond to the 7 functional groupings corresponding to the functional topology and one nuisance class. In this example, the nuisance class portion of training data is constructed with 6 ROIs located at population-level average cerebrospinal fluid regions in the brain. The nuisance class represents estimates for voxels to be of non-interest for functional connectivity mapping, given that correlation patterns in cerebrospinal fluid regions do not indicate those voxels being associated with a particular brain function. The functional connectivity analysis MLP is, in some examples, nonadaptive, meaning that the connection weight files are static and not further trained during device use.

The system transforms voxel raw identify scores (raw MLP output) to functional group membership estimation percentiles. In this step, the voxel raw identity scores for class membership values are transformed to percentiles for mapping. This statistical analysis consists of first making the raw identity scores for all voxels in each class a uniform distribution from 0 to 1 to compare equal shares of voxels between functional grouping classes. This step is conducted so that the classification does not bias a particular functional grouping for a subject who theoretically has an atypical level of BOLD activation in any given functional grouping. Next, the functional grouping estimation scores for each voxel are normalized such that they sum to unity, so that the classification purposefully biases voxels which are indicated for membership in overwhelmingly one functional grouping. Finally, the functional grouping estimation scores for all voxels in each class are again transformed to a uniform distribution from 0 to 1, in this case so that the class membership estimation value for each voxel is a percentile value.

The functional connectivity maps are unlabeled as to their specific functions. The final output of the functional connectivity analysis is a 4 dfp formatted image with seven frames, one for each functional grouping class. In each image frame, non-brain voxels have an intensity value of 0, and brain voxels have an intensity value equivalent to the voxel's membership estimation percentile for the corresponding functional grouping class. This output is utilized by the functional connectivity processing component in generating the unlabeled functional connectivity maps.

In some examples, the functional connectivity processing component does not display the unlabeled functional connectivity maps and reference location maps as viewable images. It only generates output data in standard DICOM® format for display outside of the computing device or other computing platform hosting the functional connectivity processing component. Therefore, the visual of the functional connectivity map and/or the reference location map overlaid on a structural MRI is displayed or otherwise generated using DICOM® image viewing software on the image generation device, such as the image generation device 214 in FIG. 2 and FIG. 3. Exemplary images of functional connectivity maps overlaid on a subject's structural MRI are shown in FIG. 8 through FIG. 14 below.

Figure 8:
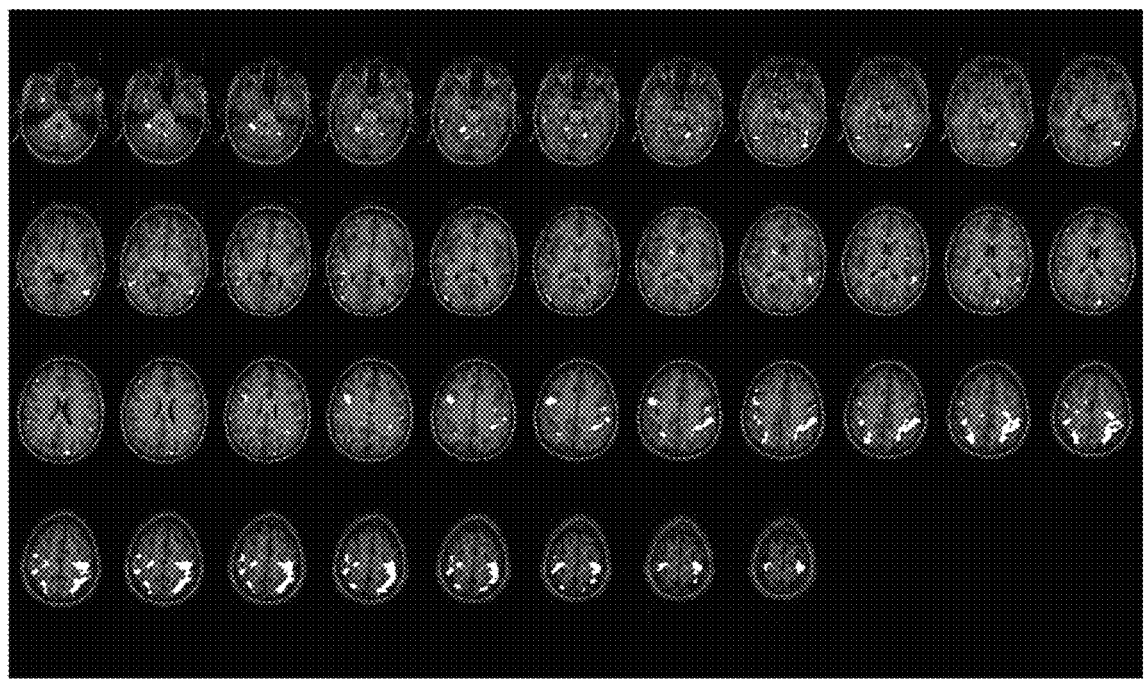
FIG. 8 is an exemplary functional connectivity map.

FIG. 8 is an exemplary functional connectivity map showing forty-one transverse slices of a subject's brain from bottom to top, with functionally connected voxels highlighted with a white overlay on the subject's structural brain image. The image output includes all voxels in a functionally connected grouping for which a confidence measure is within a range from 0.97 to 1.0. Given the structural location of the voxels shown, a trained radiologist or other trained imaging technician can recognize, even without labeling, that the functional connectivity map is of the individual subject's dorsal attention network (DAN).

Figure 9:
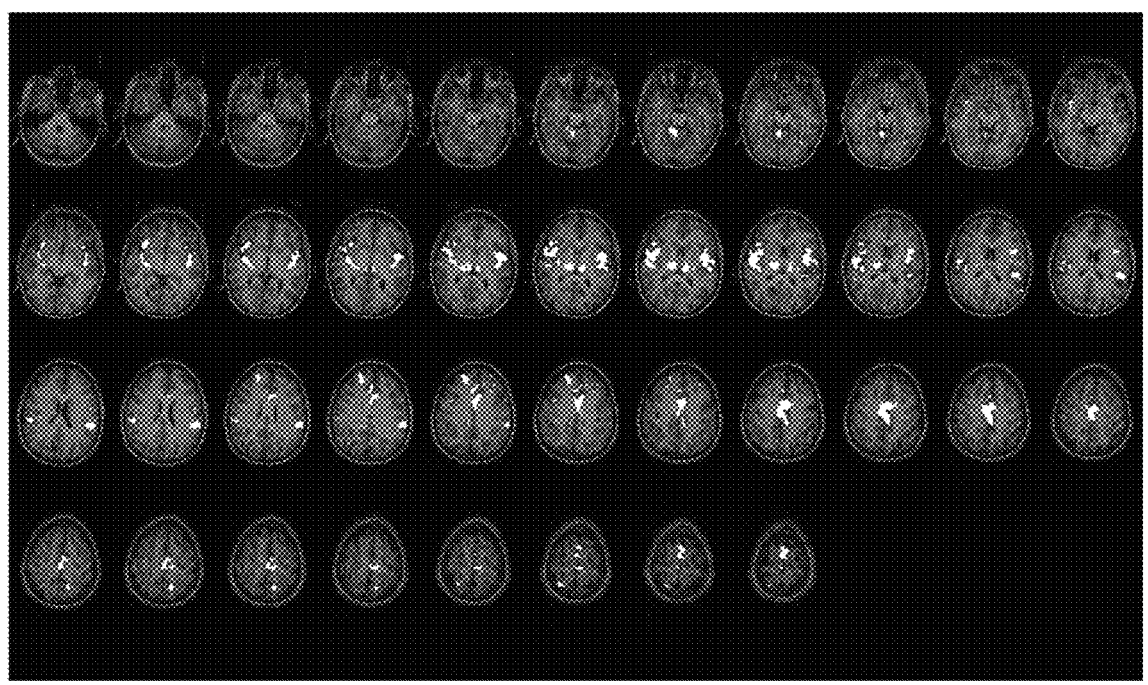
FIG. 9 is an exemplary second functional connectivity map.

FIG. 9 is an exemplary second functional connectivity map showing forty-one transverse slices of a subject's brain from bottom to top, with functionally connected voxels highlighted with a white overlay on the subject's structural brain image. In this example, the structural location of the voxels shown in the unlabeled functional connectivity map indicate this is the individual subject's ventral attention network (VAN).

Figure 10:
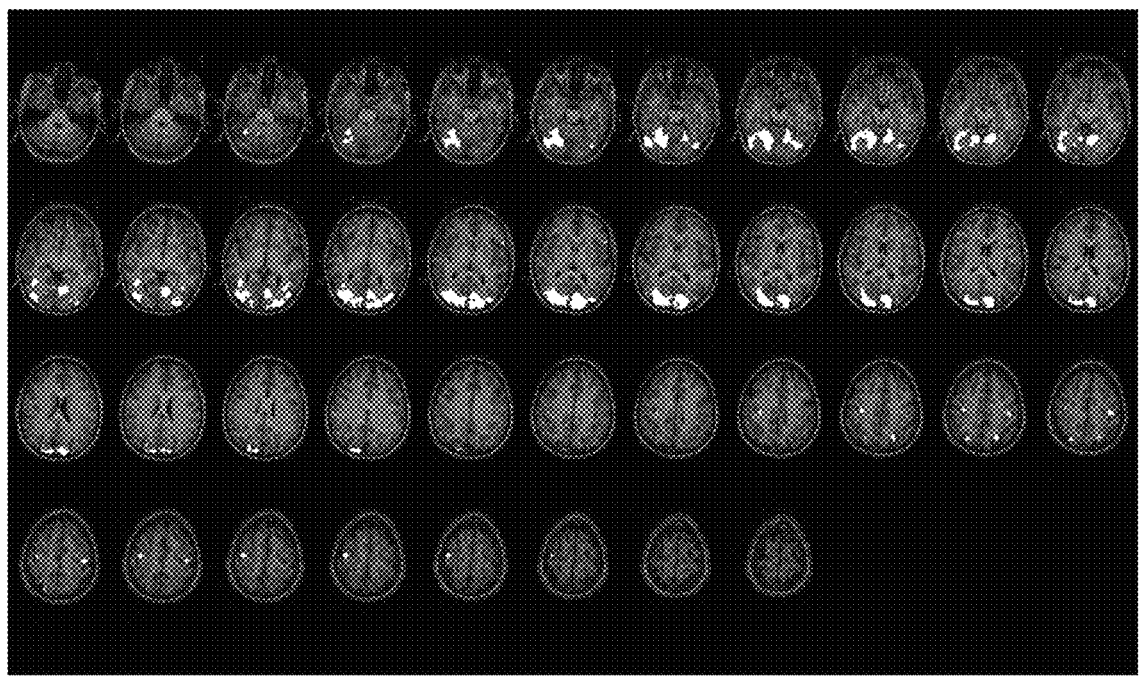
FIG. 10 is an exemplary third functional connectivity map.

FIG. 10 is an exemplary third functional connectivity map showing forty-one transverse slices of a subject's brain from bottom to top, with functionally connected voxels highlighted with a white overlay on the subject's structural brain image. Given the structural location of the voxels shown, a user can recognize, even without labeling, that the functional connectivity map is of the individual subject's visual network (VIS).

Figure 11:
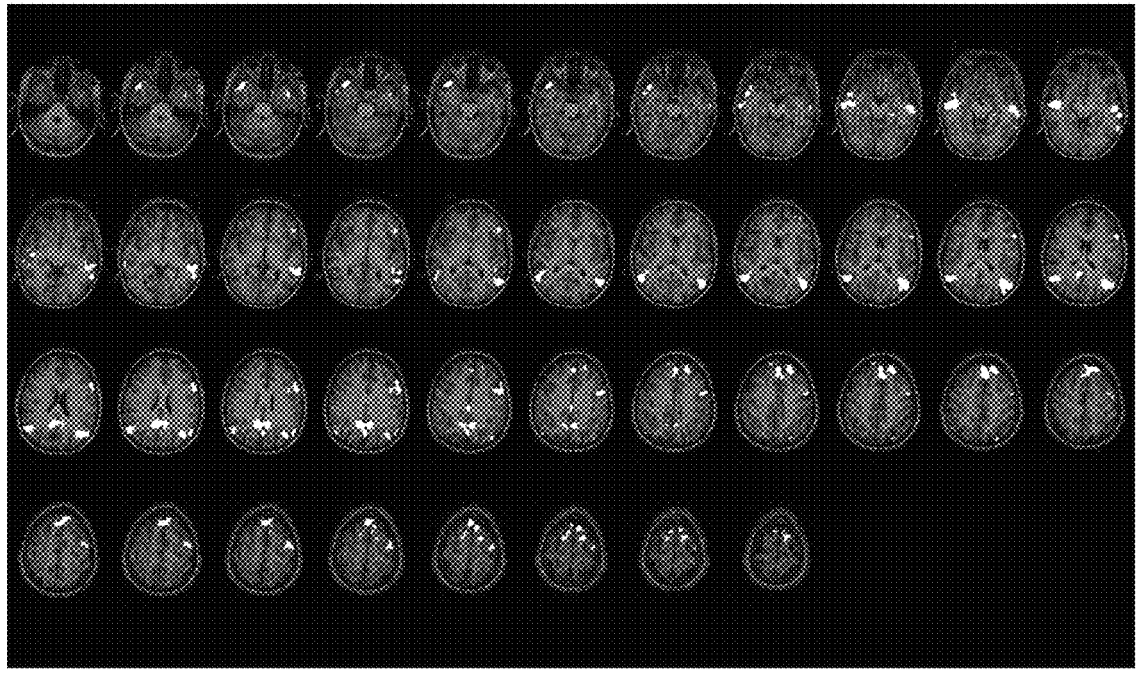
FIG. 11 is an exemplary fourth functional connectivity map.

FIG. 11 is an exemplary fourth functional connectivity map showing forty-one transverse slices of a subject's brain from bottom to top, with functionally connected voxels highlighted with a white overlay on the subject's structural brain image. Given the structural location of the voxels, in this example, the functional connectivity map connected voxels correspond with the individual subject's default mode network (DMN).

Figure 12:
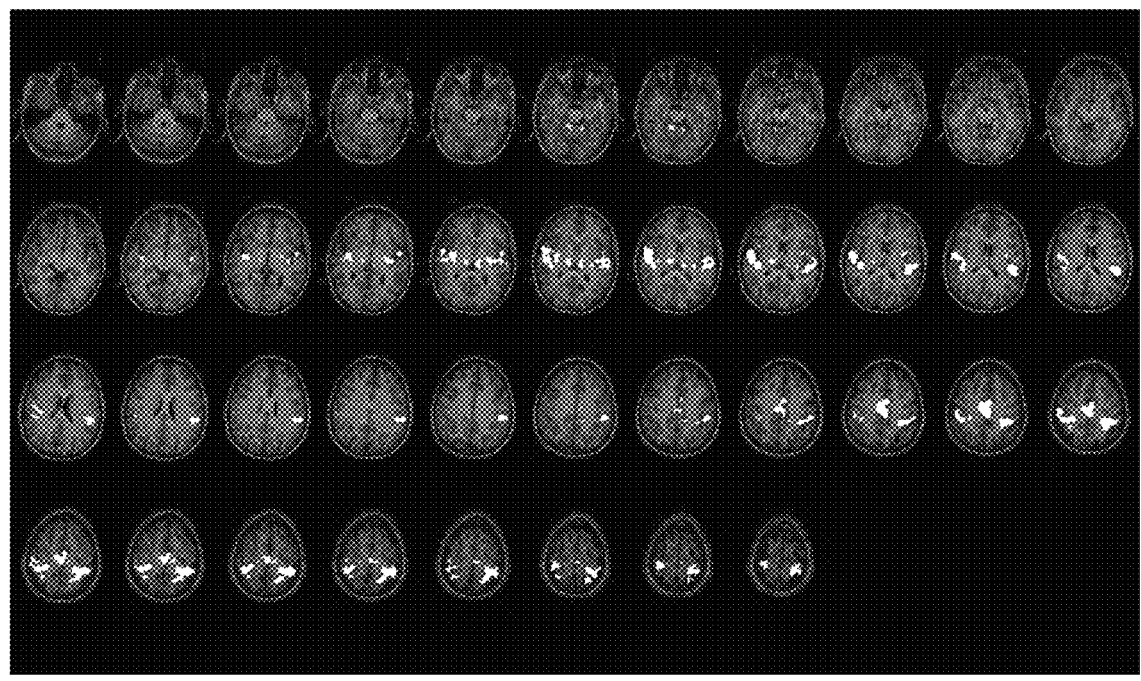
FIG. 12 is an exemplary fifth functional connectivity map.

FIG. 12 is an exemplary fifth functional connectivity map showing a set of transverse slices of a subject's brain from bottom to top. The functionally connected voxels, highlighted with a white overlay on the subject's structural brain image, are consistent with a sensorimotor network (SMN).

Figure 13:
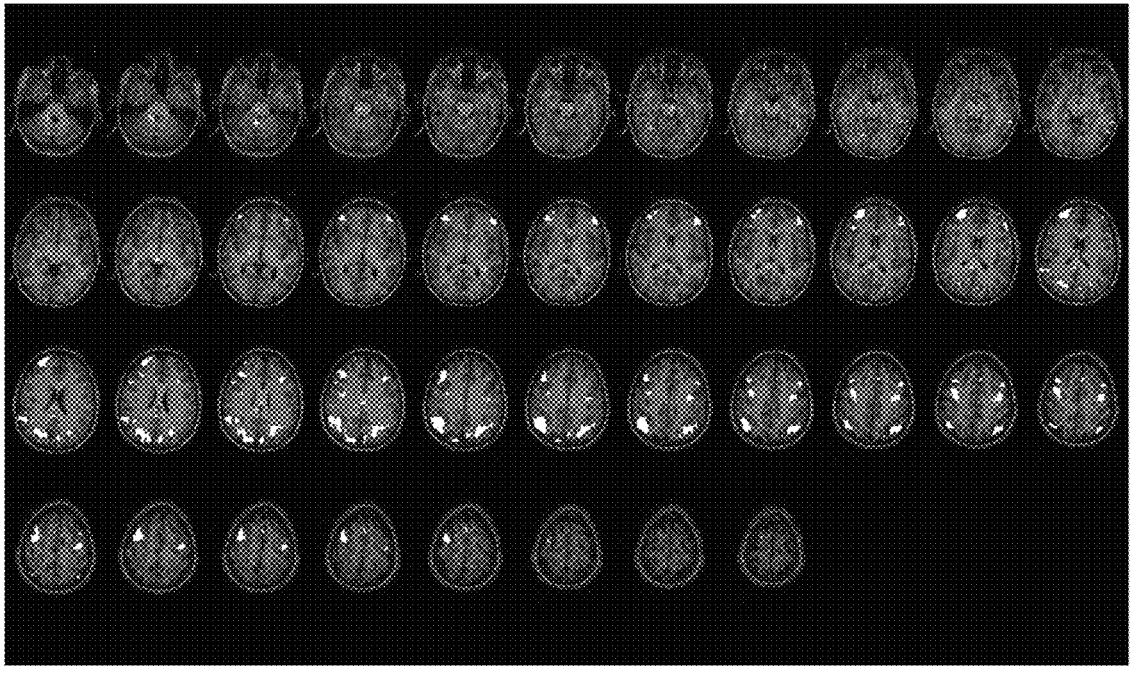
FIG. 13 is an exemplary sixth functional connectivity map.

FIG. 13 is an exemplary sixth functional connectivity map showing forty-one transverse slices of a subject's brain. The functionally connected voxels are highlighted with a white overlay on the subject's structural MRI brain image. The image output includes all voxels in a functionally connected grouping for which a confidence measure is within a threshold range. In this non-limiting example, the threshold range is from 0.97 to 1.0. Given the structural location of the voxels shown in the unlabeled functional connectivity map, a trained user can determine this exemplary functional connectivity map is of the individual subject's frontoparietal control network (FPC).

Figure 14:
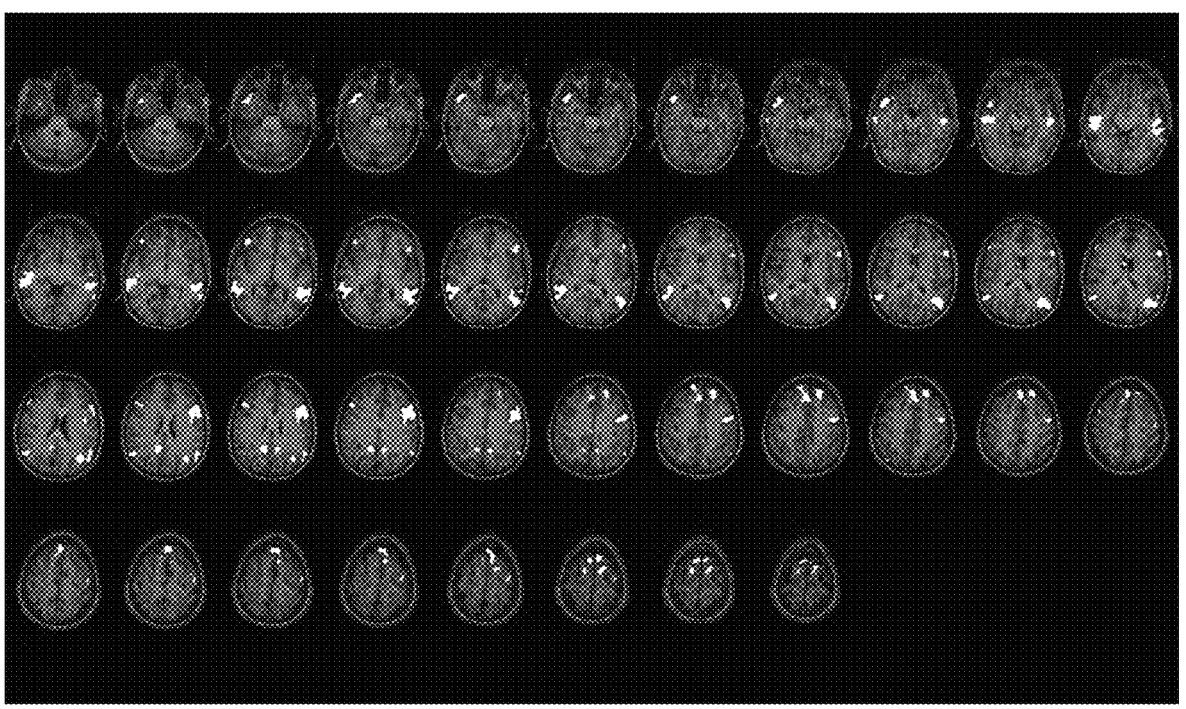
FIG. 14 is an exemplary seventh functional connectivity map.

FIG. 14 is an exemplary seventh functional connectivity map showing a plurality of transverse slices of a subject's brain from bottom to top, with functionally connected voxels highlighted with a white overlay on the subject's structural MRI brain image. The image output includes one or more voxels in a functionally connected grouping having a threshold confidence measure. In this example, the unlabeled functional connectivity map can be determined to be of the individual subject's language network (LAN).

In FIG. 8-FIG. 14, the subject is an individual patient. In other examples, the structural MRI brain image is of a representative subject derived from an aggregate of a plurality of subjects.

In some examples, a separate set of reference location maps is also generated, as reference information. The reference location maps provide reference locations for each of the predefined resting state brain networks.

The set of reference location maps, in some examples, include a set of seven reference location maps showing population-level reference locations (also called "regions of interest," or "ROIs") for each of the seven major brain functions, shown above in FIG. 8-FIG. 14. The reference locations are superimposed upon the subject's structural brain MRI image and provided in standard DICOM® format. The reference locations define points within a normalized brain atlas that are consistently identified at a population level as being members of the functional network for the seven brain functions of the brain function topology, shown above in FIG. 8-FIG. 14. These population-level reference locations (e.g., ROIs), indeed, are the same reference locations used to create machine-learning training data in the design of the functional connectivity processing component machine-learning algorithm. In the examples shown in FIG. 15-FIG. 21 below, each reference location is illustrated as a five-millimeter (5 mm) dot superimposed over each reference location on the structural brain image of the subject.

In some examples, the functional connectivity processing component machine-learning based algorithm is tuned with the training data used in its development (e.g., the reference locations) to generate an output conforming to a readily understood brain function topology. Therefore, the addition of the reference information output can be used to help trained radiologists evaluate the functional connectivity maps generated by the functional connectivity processing component. Maps of the reference location information used in the design of the functional connectivity processing component is a valuable complement to a radiologist's clinical training and knowledge for the interpretation and evaluation of the functional connectivity maps.

Figure 15:
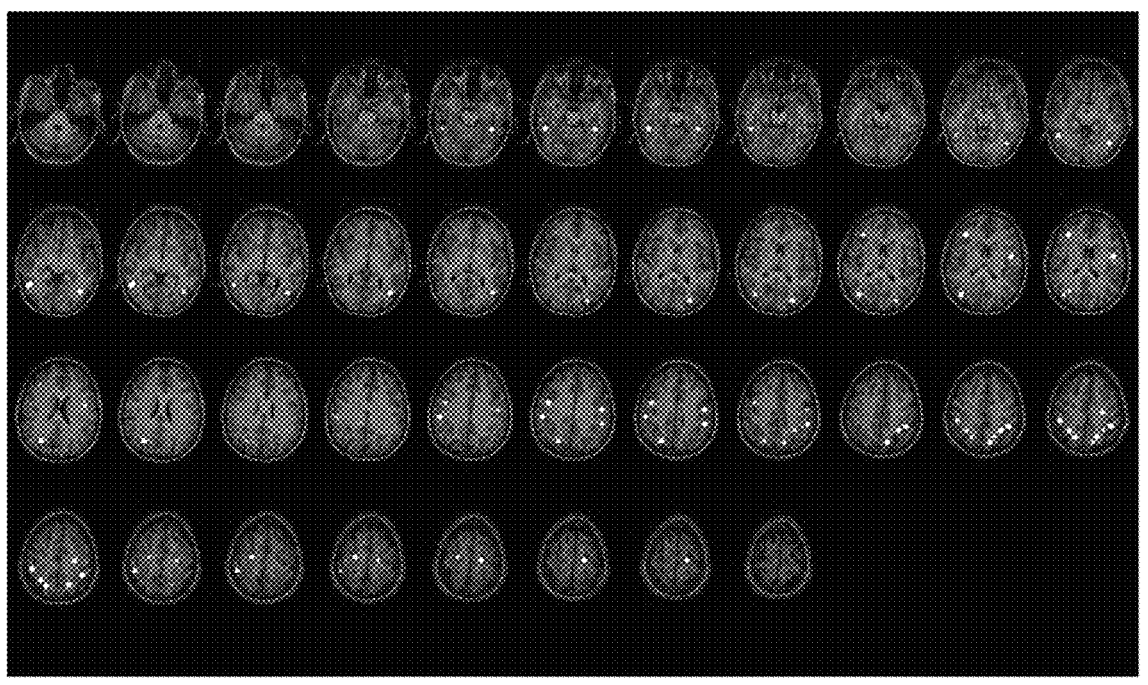
FIG. 15 is an exemplary reference location map for a dorsal attention network (DAN).

FIG. 15 is an exemplary reference location map for a dorsal attention network (DAN). The DAN is frequently involved, or recruited, in tasks requiring spatial attention, and includes the intraparietal sulcus and the frontal eye fields.

Figure 16:
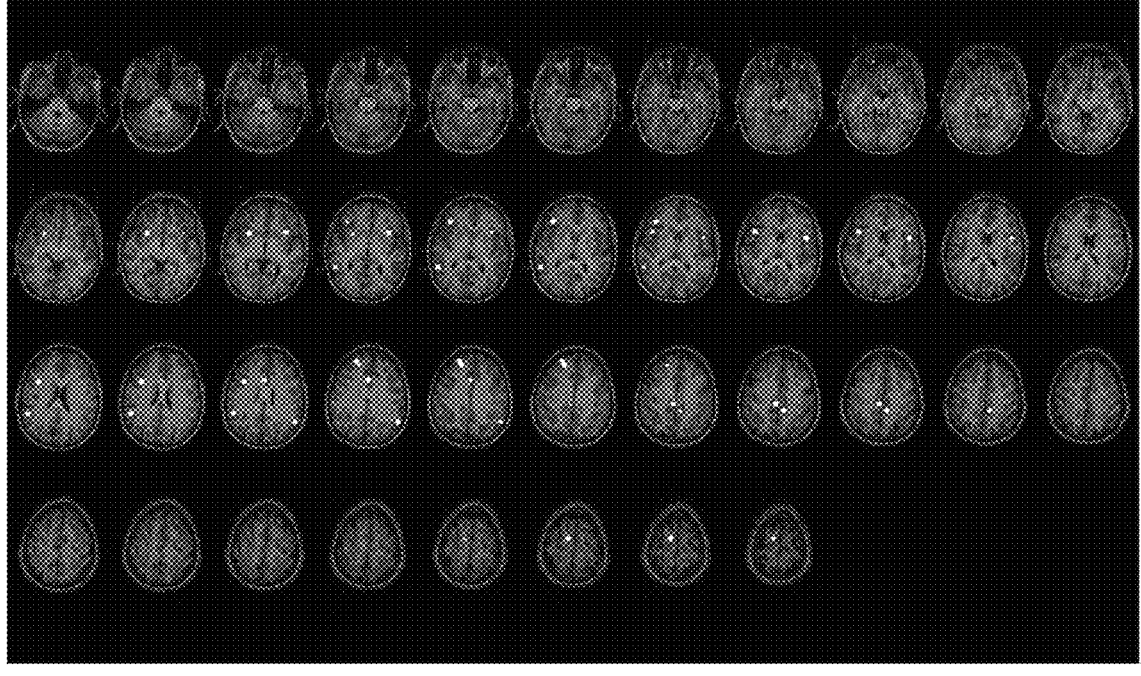
FIG. 16 is an exemplary reference location map for a ventral attention network (VAN).

FIG. 16 is an exemplary reference location map for a ventral attention network (VAN). In some examples, the VAN is involved in the detection of environmental salient events and includes the temporal-parietal junction and ventral frontal cortex. The VAN, in this topology, includes a related Cingulo-Opercular Network (CO). The inclusion of the CO in the VAN is done because the spontaneous brain activations within the CO are, on a population basis, sufficiently time correlated with those in the VAN such that collapsing the CO with the VAN into one defined functional network enables networks to be consistently revealed in a broad population of subjects. The CO network, also known as the salience network or the core control network, includes the medial superior frontal cortex, anterior insula, and anterior prefrontal cortex. The CO network is thought to enable the performance of tasks requiring executive control.

Figure 17:
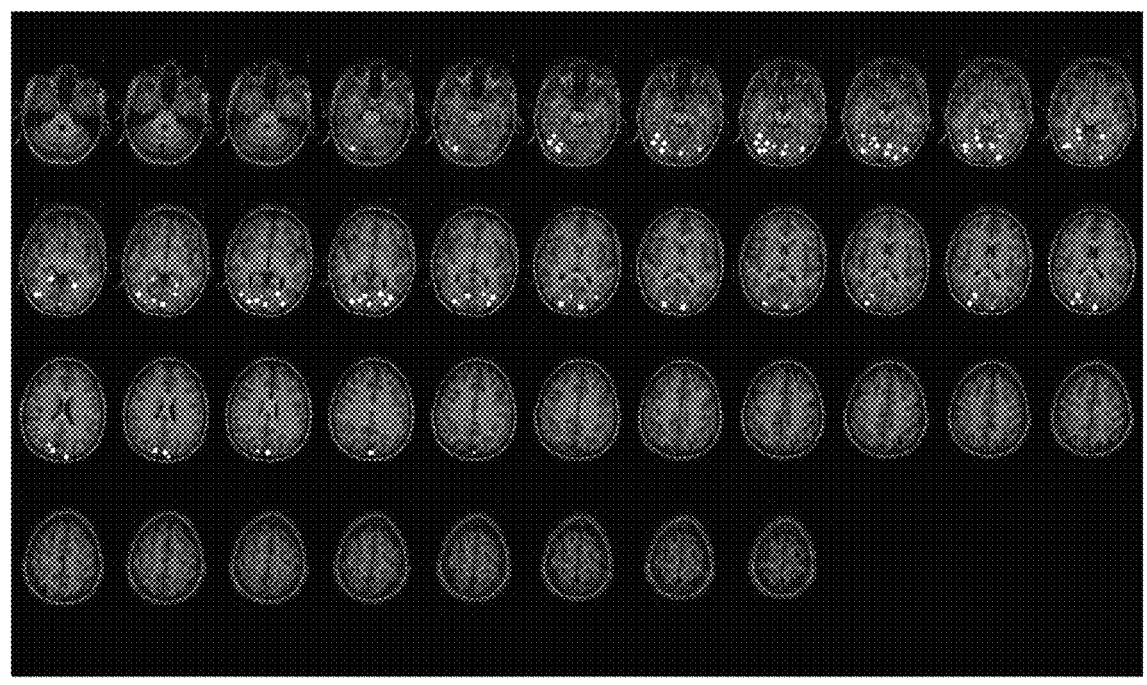
FIG. 17 is an exemplary reference location map for a visual network (VIS).

FIG. 17 is an exemplary reference location map for a visual network (VIS). The VIS is believed to be involved in vision processes and includes most of the occipital cortex, including both the striate cortex (V1, Brodmann area 17) and many extra-striate areas in the occipital lobe. The VIS occupies a large fraction of the posterior occipital cortical surface.

In this example, VIS reference location map appears using conventional DICOM® image viewing software providing image viewing capability. The VIS reference location map, in this example, shows 41 transverse slices of the subject's brain from bottom to top, with 30 reference locations for the VIS being shown. Each reference location is displayed as a 5 mm radius sphere centered upon the point of the reference location. Given the radius of these spheres and width of slices, each sphere appears on multiple adjacent slices.

Figure 18:
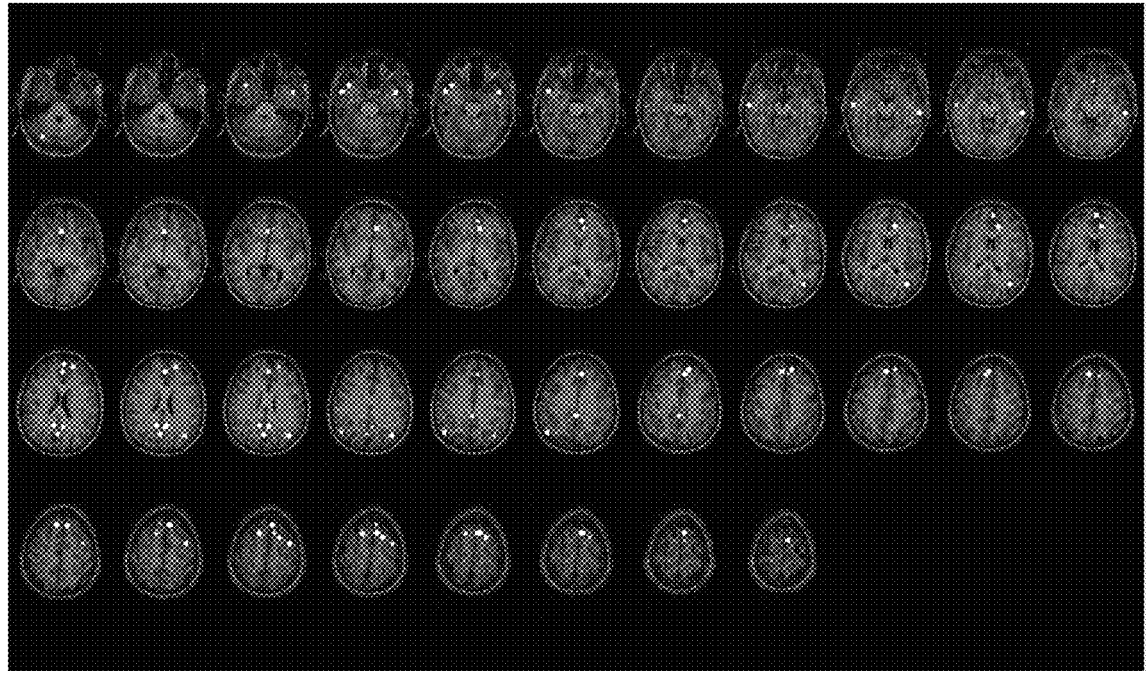
FIG. 18 is an exemplary reference location map for a default mode network (DMN).

FIG. 18 is an exemplary reference location map for a default mode network (DMN). The defining property of the DMN is that it is more active at rest than during performance of goal-directed tasks, hence, the designation, "default." Multiple high-level functions have been attributed to the DMN, which include episodic memory, prospection, and social cognition.

Figure 19:
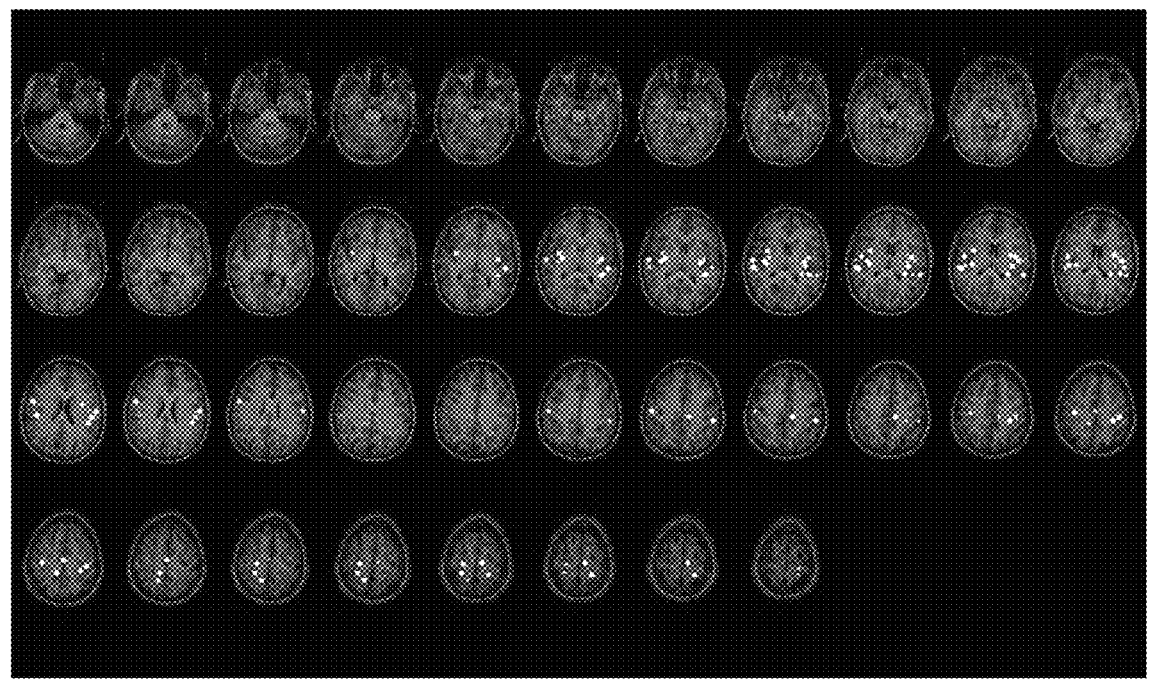
FIG. 19 is an exemplary reference location map for a sensorimotor network (SMN).

FIG. 19 is an exemplary reference location map for a sensorimotor network (SMN). The SMN is involved in motor and somatosensory processes throughout the body and encompasses primary and higher order motor and sensory areas. The locations of areas M1 and S1 (primary motor and somatosensory cortices, respectively) that are included in the SMN are very consistent across subjects in the pre- and postcentral sulcus. The SMN also includes the supplementary motor area, an area that can cause temporary motor symptoms when disrupted. The SMN, in this topology, includes the auditory network (AN), in that spontaneous brain activations within the AN are sufficiently time correlated on a population basis with those in the SMN that collapsing the AN with the SNM into one defined functional network enables networks to be consistently revealed in a broad population of subjects. The AN is involved in auditory processes and includes the Heschl gyrus (containing the primary auditory cortex), the superior temporal gyms, and the posterior insula.

Figure 20:
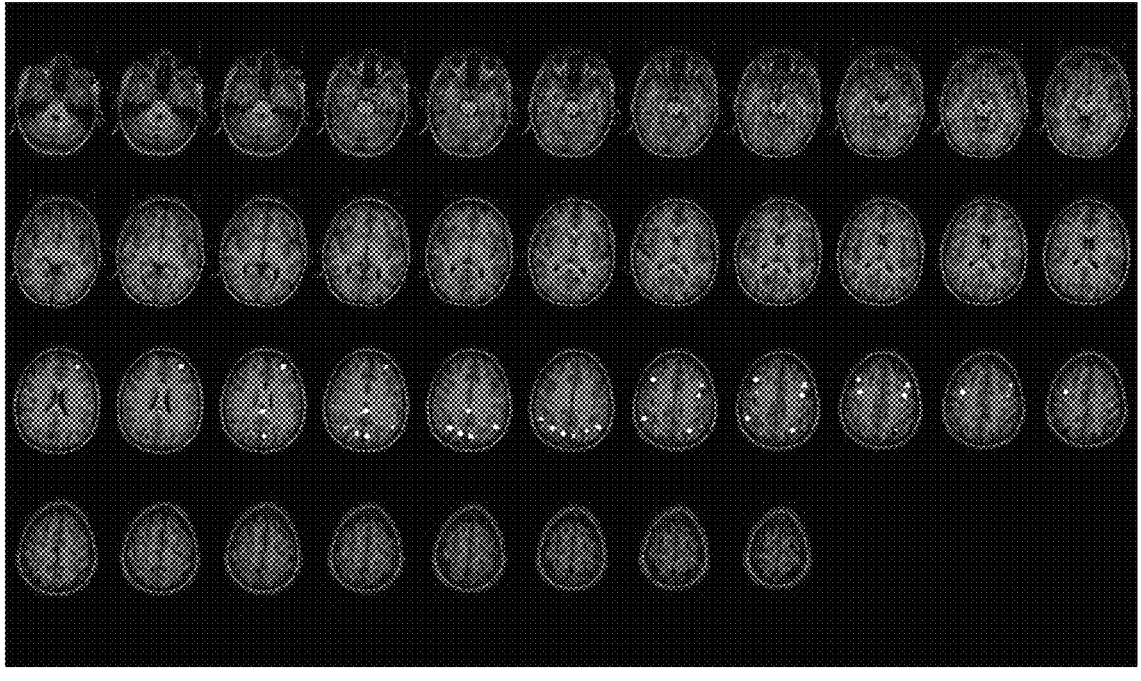
FIG. 20 is an exemplary reference location map for a frontoparietal control network (FPC).

FIG. 20 is an exemplary reference location map for a frontoparietal control network (FPC). The FPC is involved in working memory and control of goal-directed behavior and includes the lateral prefrontal cortex and the inferior parietal lobule.

Figure 21:
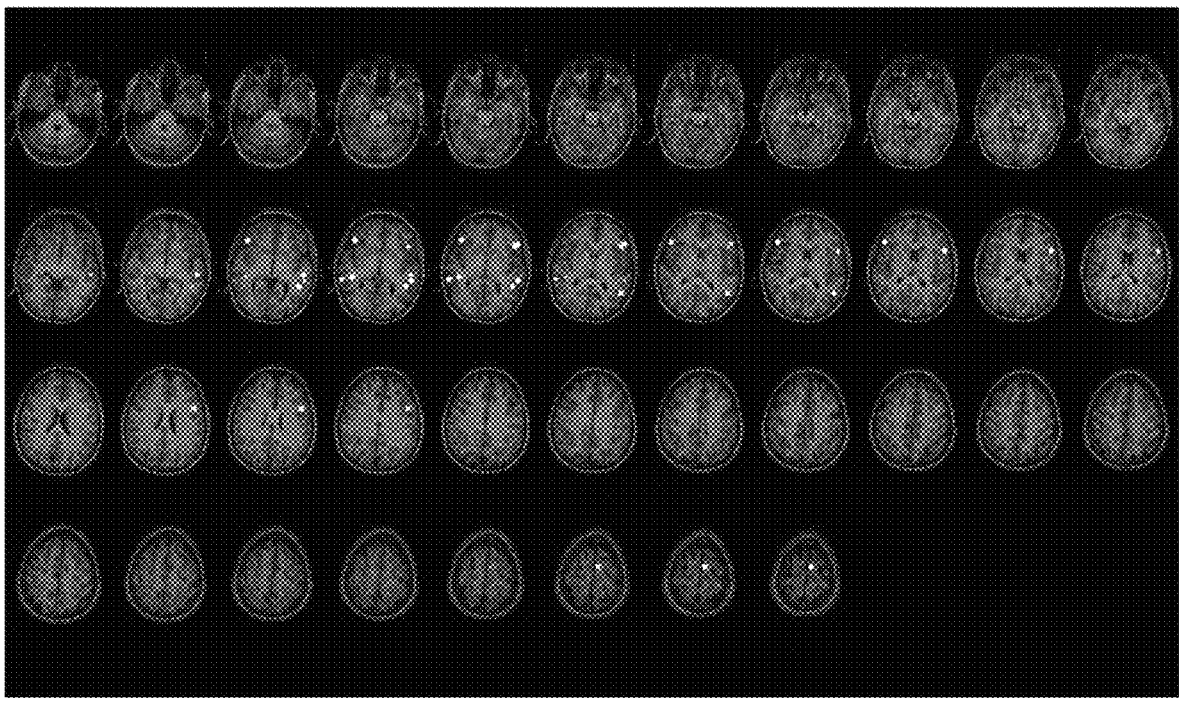
FIG. 21 is an exemplary reference location map for a language network (LAN).

FIG. 21 is an exemplary reference location map for a language network (LAN). The LAN is typically involved in language comprehension and speech generation and includes Broca's area (a key component related to word articulation and expression), Wernicke's area (which is concerned with the comprehension of language), multiple other language-related areas, and extends to prefrontal, temporal, parietal, and subcortical regions.

The development of resting state networks begins in the womb with both SMN and VIS showing adult-like topology at birth. Other networks develop rapidly after birth, such that components of the DMN, LAN, and DAN develop an adult-like topology by age one. VAN and FPC networks show much slower (although still significant) development which continues throughout childhood.

Figures 22A, 22B, 22C, 22D, 22E, 22F, 22G:
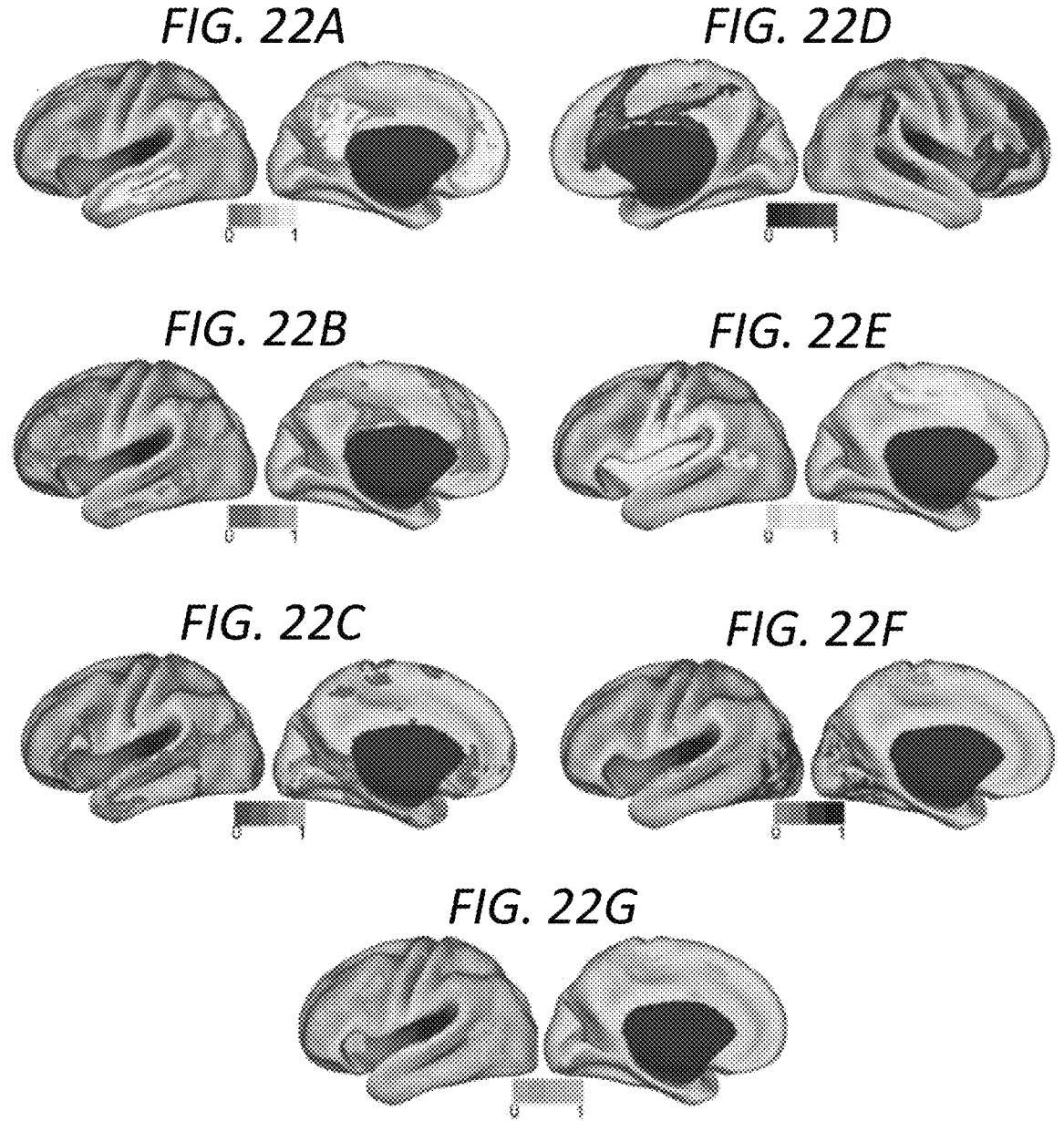
FIG. 22A to FIG. 22G illustrate exemplary brain function topology.

FIG. 22A-FIG. 22G is an exemplary brain function topology used by the functional connectivity processing component in some examples. A default mode network (DMN) is shown in FIG. 22A. FIG. 22B shows an exemplary brain function topology for a frontoparietal control network (FPC). FIG. 22C is an exemplary brain function topology for a language network (LAN). FIG. 22D is an exemplary brain function topology used by the functional connectivity processing component for a ventral attention network (VAN). The right hemisphere is displayed for the VAN because it is right lateralized. FIG. 22E is an exemplary brain function topology associated with a sensorimotor network (SMN). FIG. 22F is an exemplary brain function topology for a visual network (VIS). FIG. 22G is an exemplary brain function topology for a dorsal attention network (DAN).

The computer-implemented methods and processes described herein may include additional, fewer, or alternate actions, including those discussed elsewhere herein. The present systems and methods may be implemented using one or more local or remote processors, transceivers, and/or sensors (such as processors, transceivers, and/or sensors mounted on vehicles, stations, nodes, or mobile devices, or associated with smart infrastructures and/or remote servers), and/or through implementation of computer-executable instructions stored on non-transitory computer-readable media or medium. Unless described herein to the contrary, the various steps of the several processes may be performed in a different order, or simultaneously in some instances.

Additionally, the computer systems discussed herein may include additional, fewer, or alternative elements and respective functionalities, including those discussed elsewhere herein, which themselves may include or be implemented according to computer-executable instructions stored on non-transitory computer-readable media or medium.

The methods and systems may be implemented using computer programming or engineering techniques including computer software, firmware, hardware, or any combination or subset.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally, or alternatively, the machine learning programs may be trained by inputting sample data sets or certain data into the programs, such as images, object statistics and information, historical estimates, and/or actual repair costs. The machine learning programs may utilize deep learning algorithms that may be primarily focused on pattern recognition and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Supervised and unsupervised machine learning techniques may be used. In supervised machine learning, a processing element may include example inputs and their associated outputs and may seek to discover a general rule that maps inputs to outputs, so that when subsequent novel inputs are provided the processing element may, based upon the discovered rule, accurately predict the correct output. In unsupervised machine learning, the processing element may be used to find its own structure in unlabeled example inputs.

Based upon these analyses, the processing element may learn how to identify characteristics and patterns that may then be applied to analyzing image data, model data, and/or other data. The processing element may also learn how to identify trends that may not be readily apparent based upon collected scan data.

In the exemplary embodiment, a processing element may be instructed to execute one or more of the processes and subprocesses described above by providing the processing element with computer-executable instructions to perform such steps/sub-steps, and store collected data (e.g., trust stores, authentication information, etc.) in a memory or storage associated therewith. This stored information may be used by the respective processing elements to make the determinations necessary to perform other relevant processing steps, as described above.

The aspects described herein may be implemented as part of one or more computer components, such as a client device, system, and/or components thereof, for example. Furthermore, one or more of the aspects described herein may be implemented as part of a computer network architecture and/or a cognitive computing architecture that facilitates communications between various other devices and/or components. Thus, the aspects described herein address and solve issues of a technical nature that are necessarily rooted in computer technology.

Furthermore, the embodiments described herein improve upon existing technologies, and improve the functionality of computers, by more reliably protecting the integrity and efficiency of computer networks and the devices on those networks at the server-side, and by further enabling the easier and more efficient identification and mapping of resting state neural networks. The present embodiments therefore improve the speed, efficiency, and reliability in which such determinations and processor analyses may be performed. Due to these improvements, the aspects described herein address computer-related issues that significantly improve the efficiency of healthcare diagnostics in comparison with conventional techniques.

ADDITIONAL EXAMPLES

In some examples, a computer implemented method for generating outputs and accompanying reference information in a software-based system comprises generating a primary system output using a machine-learning based algorithm created through an algorithm training process that uses training data; and separately generating an accompanying reference output of reference information informative of the training data used to create the machine-learning based algorithm.

In some examples, a computer system comprises a processor; and a non-transitory computer readable medium having stored thereon program code executable by the processor, the program code causing the processor to: generate a primary system output using a machine-learning based algorithm created through an algorithm training process that uses training data; and separately generate an accompanying reference output of reference information informative of the training data used to create the machine-learning based algorithm.

In some examples, a non-transitory computer storage medium has stored thereon program code executable by a processor, the program code embodying a method comprising: generating a primary system output using a machine-learning based algorithm created through an algorithm training process that uses training data; and separately generating an accompanying reference output of reference information informative of the training data used to create the machine-learning based algorithm.

Alternatively, or in addition to the other examples described herein, examples include any combination of the following:

wherein the primary system output comprises a mapping of defined functional brain networks within the brain of an individual subject based upon image data pertaining to the individual subject's brain.

wherein the primary system output comprises the mapping of defined functional brain networks overlaid upon a structural image including the individual subject's brain.

wherein the reference output comprises population-averaged location information for the defined functional brain networks.

wherein the population-averaged location information for the defined functional brain networks comprises, for each defined network, a set of population-averaged reference locations falling within the bounds of the defined network.

wherein the reference output comprises the sets of population-averaged reference locations overlaid upon a structural image of a brain.

wherein the structural image of a brain upon which the sets of population-averaged reference locations are overlaid is a structural image of the brain of the individual subject.

wherein the image data are functional magnetic resonance imaging (fMRI) data.

wherein the fMRI data are resting-state fMRI (rs-fMRI) data acquired during a time the subject is in a state of rest.

wherein the functional brain networks are a defined set of one or more resting state networks (RSNs) comprising a topology of RSNs.

wherein the RSNs included in the topology are macro-scale RSNs present within a broad range of healthy subjects.

wherein the number of macro-scale RSNs included in the topology of RSNs equals six to eight RSNs.

wherein the number of macro-scale RSNs included in the topology of RSNs equals seven.

wherein the macro-scale RSNs includes brain networks making up the eloquent cortex of the subject's brain.

wherein the brain networks making up the eloquent cortex include at least a sensorimotor network (SMN) and a language network (LAN).

wherein the brain networks making up the eloquent cortex further include a vision network (VIS).

wherein the macro-scale RSNS comprises one or more of a ventral attention network (VAN), a dorsal attention network (DAN), a frontoparietal control network (FPC), and a default mode network (DMN).

wherein generating the primary system output comprises generating a set of functional connectivity maps.

wherein each functional connectivity map identifies functionally connected voxels of the individual subject's brain included in one RSN of the topology of RSNs.

wherein generating the primary system output comprises generating, based upon the rs-fMRI data for the individual subject, a voxel-wise correlation map of the individual subject's brain comprising measures of correlation between MR signals at different voxel pairs throughout the brain.

wherein generating the voxel-wise correlation map comprises calculating, for each voxel pair, a Pearson product-moment correlation coefficient for the MR signal at one voxel compared to the MR signal at a second voxel.

wherein the calculation of the correlation coefficient yields a single scalar value representing a measure of strength in linear association between the two MR signals of the voxel pair.

wherein generating the primary system output further comprises generating the set of functional connectivity maps by assigning voxels of the individual subject's brain to the defined RSNs of the topology of RSNs.

wherein the assignment of voxels to the defined RSNs involves use of the machine-learning based algorithm.

wherein the machine-learning based algorithm is trained, using a supervised learning process, to assign voxels using pattern matching that applies weight in determining the assignment to the following factors: (i) within-network MR signal patterns being correlated in time, and (ii) global patterns in MR signals throughout the brain and between different networks.

wherein the supervised learning process uses, for each RSN of the topology of RSNs, a set of reference locations in the brain representing population-based locations that fall within the RSN.

wherein the supervised learning process uses rs-fMRI datasets acquired from a number of individual subjects.

wherein the supervised learning process includes generating, based upon the rs-fMRI data of one rs-fMRI dataset, a voxel-wise correlation map of the individual subject's brain comprising measures of correlation between MR signals at different voxel pairs throughout the brain.

wherein the supervised learning process further includes generating training data for each rs-fMRI dataset that includes supervised training data comprising: (i) the voxel-wise correlation map information for voxel locations corresponding to the reference locations, and (ii) for supervision, network assignment information comprising the RSN identity to which the voxel location corresponding to the reference location is a member.

wherein the reference output comprises a set of RSN reference maps, one for each RSN of the topology of RSNs, wherein each RSN reference map includes the corresponding set of reference locations in the brain representing population-based locations that fall within the RSN.

wherein each RSN reference map comprises the reference locations for that RSN overlaid upon an anatomical brain image.

wherein the anatomical brain image upon with the RSN reference locations are overlaid is an anatomical brain image of the same individual subject for which output RSN mappings are generated.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a programmable logic unit (PLU), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

The computer-implemented methods discussed herein may include additional, less, or alternate actions, including those discussed elsewhere herein. The methods may be implemented via one or more local or remote processors, transceivers, servers, and/or sensors, and/or via computer-executable instructions stored on non-transitory computer-readable media or medium.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As used herein, the terms "about," "substantially," "essentially" and "approximately" when used in conjunction with ranges of dimensions, concentrations, temperatures or other physical or chemical properties or characteristics is meant to cover variations that may exist in the upper and/or lower limits of the ranges of the properties or characteristics, including, for example, variations resulting from rounding, measurement methodology or other statistical variation.

When introducing elements of the present disclosure or the embodiment(s) thereof, the articles "a," "an," "the," and "said" are intended to mean that there are one or more of the elements. The terms "comprising," "including," "containing," and "having" are intended to be inclusive and mean that there may be additional elements other than the listed elements. The use of terms indicating a particular orientation (e.g., "top," "bottom," "side," etc.) is for convenience of description and does not require any particular orientation of the item described. As various changes could be made in the above constructions and methods without departing from the scope of the disclosure, it is intended that all matter contained in the above description and shown in the accompanying drawing[s] shall be interpreted as illustrative and not in a limiting sense.

What is claimed is:

1. A computer implemented method for generating outputs and accompanying reference information in a software-based system, comprising:
generating a primary system output using a machine-learning based algorithm created through an algorithm training process that uses training data, wherein the primary system output comprises a mapping of defined functional brain networks within a brain of an individual subject based upon image data pertaining to the brain of the individual subject; and
separately generating an accompanying reference output of reference information informative of the training data used to create the machine-learning based algorithm, wherein the reference output comprises population-averaged location information for the defined functional brain networks.

2. The computer implemented method of claim 1, wherein the primary system output comprises the mapping of defined functional brain networks overlaid upon a structural image including the brain of the individual subject.

3. The computer implemented method of claim 1, wherein the population-averaged location information for the defined functional brain networks comprises, for each defined network, a set of population-averaged reference locations falling within bounds of that defined network, wherein the reference output comprises the sets of population-averaged reference locations overlaid upon a structural image of a brain, and wherein the structural image of the brain upon which the sets of population-averaged reference locations are overlaid is a structural image of the brain of the individual subject.

4. The computer implemented method of claim 1, wherein the image data are functional magnetic resonance imaging (fMRI) data, wherein the fMRI data are resting-state fMRI (rs-fMRI) data acquired during a time the individual subject is in a state of rest, wherein the functional brain networks are a defined set of one or more resting state networks (RSNs) comprising a topology of RSNs, and wherein the RSNs included in the topology are macro-scale RSNs present within a broad range of healthy subjects.

5. The computer implemented method of claim 4, wherein a number of macro-scale RSNs included in the topology of RSNs equals six to eight RSNs.

6. The computer implemented method of claim 4, wherein the macro-scale RSNs include brain networks making up an eloquent cortex of the brain of the individual subject, wherein the brain networks making up the eloquent cortex include at least a sensorimotor network (SMN) and a language network (LAN), wherein the brain networks making up the eloquent cortex further include a vision network (VIS).

7. The computer implemented method of claim 4, wherein the macro-scale RSNs comprise one or more of: a ventral attention network (VAN), a dorsal attention network (DAN), a frontoparietal control network (FPC), and a default mode network (DMN).

8. The computer implemented method of claim 4, wherein generating the primary system output comprises generating a set of functional connectivity maps, and wherein each functional connectivity map identifies functionally connected voxels of the brain of the individual subject included in one RSN of the topology of RSNs.

9. The computer implemented method of claim 8, wherein generating the primary system output comprises generating, based upon the rs-fMRI data for the individual subject, a voxel-wise correlation map of the brain of the individual subject comprising measures of correlation between MR signals at different voxel pairs throughout the brain, wherein generating the voxel-wise correlation map comprises calculating, for each voxel pair, a Pearson product-moment correlation coefficient for an MR signal at one voxel compared to an MR signal at a second voxel, wherein the calculation of the correlation coefficient yields a single scalar value representing a measure of strength in linear association between the two MR signals of the voxel pair.

10. The computer implemented method of claim 8, wherein generating the primary system output further comprises generating the set of functional connectivity maps by assigning voxels of the brain of the individual subject to the defined set of one or more RSNs of the topology of RSNs, wherein the assignment of voxels to the defined set of one or more RSNs involves use of the machine-learning based algorithm, wherein the machine-learning based algorithm is trained, using a supervised learning process, to assign voxels using pattern matching that applies weight in determining the assignment to the following factors: within-network MR signal patterns being correlated in time, and global patterns in MR signals throughout the brain and between different networks.

11. The computer implemented method of claim 10, wherein the supervised learning process uses, for each RSN of the topology of RSNs, a set of reference locations in the brain representing population-based locations that fall within the RSN, and wherein the supervised learning process uses rs-fMRI datasets acquired from a number of individual subjects.

12. The computer implemented method of claim 11, wherein the supervised learning process includes generating, based upon the rs-fMRI data of one rs-fMRI dataset, a voxel-wise correlation map of the brain of the individual subject comprising measures of correlation between MR signals at different voxel pairs throughout the brain, and wherein the supervised learning process further includes generating training data for each rs-fMRI dataset that includes supervised training data comprising: the voxel-wise correlation map for voxel locations corresponding to the reference locations, and for supervision, network assignment information comprising a RSN identity to which the voxel location corresponding to the reference location is a member.

13. The computer implemented method of claim 11, wherein the reference output comprises a set of RSN reference maps, one for each RSN of the topology of RSNs, wherein each RSN reference map includes the corresponding set of reference locations in the brain representing population-based locations that fall within the RSN.

14. The computer implemented method of claim 13, wherein each RSN reference map comprises the reference locations for that RSN overlaid upon an anatomical brain image, and wherein the anatomical brain image upon which the reference locations for that RSN are overlaid is an anatomical brain image of the same individual subject for which output RSN mappings are generated.

15. A computer system comprising:

a processor; and a non-transitory computer readable medium having stored thereon program code executable by the processor, the program code causing the processor to:

generate a primary system output using a machine-learning based algorithm created through an algorithm training process that uses training data, wherein the primary system output comprises a mapping of defined functional brain networks within a brain of an individual subject based upon image data pertaining to the brain of the individual subject; and separately generate an accompanying reference output of reference information informative of the training data used to create the machine-learning based algorithm, wherein the reference output comprises population-averaged location information for the defined functional brain networks.

16. The computer system of claim 15, wherein the primary system output comprises a functional connectivity map of resting state networks derived from functional magnetic resonance imaging (fMRI) data, wherein the primary system output is overlaid on a structural magnetic resonance imaging (MRI) image of the brain of the individual subject.

17. The computer system of claim 15, wherein the reference output comprises statistical population-averaged location information for the defined functional brain networks.

18. A non-transitory computer storage medium having stored thereon program code executable by a processor, the program code embodying a method comprising:

generating a primary system output using a machine-learning based algorithm created through an algorithm training process that uses training data, wherein the primary system output comprises a mapping of defined functional brain networks within a brain of an individual subject based upon image data pertaining to the brain of the individual subject; and separately generating an accompanying reference output of reference information informative of the training data used to create the machine-learning based algorithm, wherein the reference output comprises population-averaged location information for the defined functional brain networks.

19. The computer storage medium of claim 18, wherein the primary system output comprises a functional connectivity map of resting state networks derived from functional magnetic resonance imaging (fMRI) data, wherein the primary system output is overlaid on a structural magnetic resonance imaging (MRI) image of the brain of the individual subject.

20. The computer storage medium of claim 18, wherein the reference output comprises baseline information for the defined functional brain networks associated with a healthy subject.

* * * * *